United States Patent
Thompson

(10) Patent No.: US 10,881,686 B2
(45) Date of Patent: Jan. 5, 2021

(54) COMPOSITIONS AND METHODS FOR TREATING AND PREVENTING PROTEINURIA AND ENDOTHELIAL EROSION

(71) Applicant: Zeta Biolongevity, Inc., Austin, TX (US)

(72) Inventor: Randal C. Thompson, Austin, TX (US)

(73) Assignee: ZETA BIOLONGEVITY, INC, Austin, TX (US)

( * ) Notice: Subject to any disclaimer, the term of this patent is extended or adjusted under 35 U.S.C. 154(b) by 233 days.

(21) Appl. No.: 16/173,475

(22) Filed: Oct. 29, 2018

(65) Prior Publication Data
US 2019/0167715 A1  Jun. 6, 2019

Related U.S. Application Data

(60) Provisional application No. 62/578,076, filed on Oct. 27, 2017.

(51) Int. Cl.
*A61P 13/12* (2006.01)
*A61K 33/14* (2006.01)
(Continued)

(52) U.S. Cl.
CPC ............ *A61K 33/14* (2013.01); *A61K 31/10* (2013.01); *A61K 31/194* (2013.01);
(Continued)

(58) Field of Classification Search
None
See application file for complete search history.

(56) References Cited

U.S. PATENT DOCUMENTS 5,547,945 A   8/1996  Ye et al.
5,973,011 A  10/1999  Noack et al.
(Continued)

FOREIGN PATENT DOCUMENTS

WO   2011160184 A1   12/2011

OTHER PUBLICATIONS

Butawan et al., "Methylsulfonylmethane: Applications and Safety of a Novel Dietary Supplement", Nutrients. Mar. 16, 2017;9(3). pii: E290. doi: 10.3390/nu9030290.
(Continued)

*Primary Examiner* — Erin M. Bowers
(74) *Attorney, Agent, or Firm* — Kurt T. Mulville; VLP Law Group, LLP

(57) ABSTRACT

In some embodiments, a system and/or method may inhibit and/or ameliorate proteinuria and related comorbidities in a subject. In some embodiments, proteinuria and/or Endothelial Erosion (EE) and related comorbidities may be inhibited and/or ameliorated by maximizing a subject's serum zeta potential. A subject's serum zeta potential may be maximized by administering pharmaceutical compositions which: optimize the negative electrical surface charges of a subject's blood cells, plasma proteins, and/or endothelial surface layer; optimize the composition of a subject's bloodstream (e.g., ionic strength and ion concentrations), and/or optimize the properties of the subject's bloodstream (e.g., serum pH). In some embodiments, Proteinuria and/or EE and related comorbidities may be inhibited and/or ameliorated by: maximizing a subject's serum zeta potential; repairing damage to the endothelial surface layer in a subject; making up for a subject's urinary losses of plasma proteins; and/or optimizing blood flow and facilitating healing of damage caused by Proteinuria and/or EE.

10 Claims, 20 Drawing Sheets

(51) Int. Cl.

| | |
|---|---|
| A61K 31/10 | (2006.01) |
| A61K 31/198 | (2006.01) |
| A61K 31/7008 | (2006.01) |
| A61K 31/728 | (2006.01) |
| A61K 31/737 | (2006.01) |
| A61K 36/63 | (2006.01) |
| A61K 45/06 | (2006.01) |
| A61K 31/194 | (2006.01) |
| A61K 31/355 | (2006.01) |
| A61K 33/06 | (2006.01) |
| A61K 31/353 | (2006.01) |
| A61K 33/00 | (2006.01) |
| A61K 38/40 | (2006.01) |
| A61K 38/48 | (2006.01) |

(52) U.S. Cl.
CPC .......... A61K 31/198 (2013.01); A61K 31/353 (2013.01); A61K 31/355 (2013.01); A61K 31/7008 (2013.01); A61K 31/728 (2013.01); A61K 31/737 (2013.01); A61K 33/00 (2013.01); A61K 33/06 (2013.01); A61K 36/63 (2013.01); A61K 38/40 (2013.01); A61K 38/482 (2013.01); A61K 45/06 (2013.01); A61P 13/12 (2018.01); C12Y 304/21062 (2013.01)

(56) References Cited

U.S. PATENT DOCUMENTS

| | | |
|---|---|---|
| 6,445,945 B1 | 9/2002 | Arsenault |
| 6,596,708 B1 | 7/2003 | Petrus |
| 6,797,705 B2 | 9/2004 | Daniels |
| 6,924,110 B2 | 8/2005 | Antignac et al. |
| 6,930,099 B2 | 8/2005 | Petrus |
| 6,977,168 B2 | 12/2005 | Cheung |
| 7,025,726 B2 | 4/2006 | Porter et al. |
| 7,297,556 B2 | 11/2007 | Tomosugi |
| 7,388,086 B2 | 6/2008 | Antignac et al. |
| 7,410,983 B2 | 8/2008 | Watts et al. |
| 7,749,711 B2 | 7/2010 | Le et al. |
| 7,846,914 B2 | 12/2010 | Petrus |
| 7,956,035 B2 | 6/2011 | Stroes |
| 8,017,657 B1 | 9/2011 | Petrus |
| 8,334,259 B2 | 12/2012 | Carney et al. |
| 8,486,889 B1 | 7/2013 | Petrus |
| 8,557,962 B2 | 10/2013 | Stroes |
| 8,802,162 B2 | 8/2014 | Greco |
| 8,877,239 B2 | 11/2014 | Settineri et al. |
| 9,139,629 B2 | 9/2015 | Chugh |
| 2004/0098062 A1 | 5/2004 | Nachum |
| 2005/0112123 A1 | 5/2005 | Vaughan |
| 2007/0148187 A1 | 6/2007 | Scivoletto |
| 2010/0099719 A1 | 4/2010 | Shi |
| 2012/0040014 A1 | 2/2012 | Settineri et al. |
| 2015/0366814 A1 | 12/2015 | Hu et al. |

OTHER PUBLICATIONS

Aguirre et al., "An Assessment of the Ocular Safety of Excipient Maleic Acid Following Intravitreal Injection in Rabbits", Toxicologic Pathology, 40: 797-806, 2012, pp. 797-806.
Allen et al., "Recurrent glomerulonephritis after kidney transplantation: risk factors and allograft outcomes", Kidney International (2017) 92, 461-469.
Ando et al., "Evidence for Accumulation of Lipid Hudroperoxides during the Aging of Human Red Blood Cells in the Circulation", Biol. Pharm. Bull 18(5) 1995, pp. 659-663.
Balakumar et al., "Experimental models for nephropathy", SAGE Publications 2008, pp. 189-195.
Brimble et al., "Effect of chronic kidney disease on red blood cell rheology", Clinical Hemorheology and Microcirculation 34 (2006) 411-420.
Chappell et al., "The Glycocalyx of the Human Umbilical Vein Endothelial Cell an Impressive Structure Ex Vivo but Not in Culture", Circulation Research, 2009, pp. 1313-1317.
Charradi et al., "High-fat diet induced an oxidative stress in white adipose tissue and disturbed plasma transition metals in rat: prevention by grape seed and skin extract", J Physiol Sci (2013) 63: 445-455.
Clerico et al., "Exercise-Induced Proteinuria in Well-Trained Athletes", Clin. Chem. 36/3, 562-564 (1990).
Comporti et al., "Ethanol-induced oxidative stress: basic knowledge", Genes Nutr (2010) 5: 101-109.
Currie et al., "Proteinuria and its relation to cardiovascular disease", International Journal of Nephrology and Renovascular Disease 2014:7 13-24.
Dane et al., "A microscopic view on the renal endothelial glycocalyx", Am J Physiol Renal Physiol (Feb. 11, 2015).
Drummond et al., "Structural Basis for Reduced Glomerular Filtration Capacity in Nephrotic Humans", J. Clin. Invest., vol. 94, Sep. 1994, pp. 1187-1195.
Du et al., "Oxidative Stress during Acetaminophen Hepatotoxicity: Sources, Pathophysiological Role and Therapeutic Potential", Redox Biology 114 R1, 2016.
Ebong et al., "Imaging the Endothelial Glycocalyx In Vitro by Rapid Freezing/Freeze Substitution Transmission Electron Microscopy", Arterioscler Thromb Vasc Biol, 2011, 1908-1915.
Ercal et al., "Toxic Metals and Oxidative Stress Part I: Mechanisms Involved in Metal induced Oxidative Damage", Current Topics in Medicinal Chemistry 2001, 1, 529-539.
Farquhar et al., "Glomerular Permeability", Journal of Experimental Medicine vol. 113, 1961.
Garg et al., "Glomerular Proteinuria: A complex interplay between unique players", Adv Chronic Kidney Dis. Jul. 2011 ; 18(4): 233-242.
Grossin et al., "Red blood cell adhesion in diabetes mellitus is mediated by advanced glycation end product receptor and is modulated by nitric oxide", Biorheology 46 (2009) 63-72.
Hausmann, et al., "Electrical Forces Determine Glomerular Permeability", J Am Soc Nephrol 21: 2053-2058, 2010.
Jiang et al., "Role of STAT1 and Oxidative Stress in Gentamicin-Induced Hair Cell Death in Organ of Corti", Otology & Neurotology, 37:1449-1456, 2016.
Kang et al., "The Endothelial Glycocalyx: Visualization and Measurement", Journal of Biomedicine 2017; 2: 120-123.
Kuzmuk et al., "Pigs as a Model for Biomedical Sciences", CAB International 2011. The Genetics of the Pig, 2nd Edn (eds M.F. Rothschild and A. Ruvinsky).
Lam et al., "Outpatient Management of Chronic Kidney Disease: Proteinuria, Anemia and Bone Disease as Therapeutic Targets", DM, Apr. 2010.
Majerczak et al., "Endothelial Glycocalyx Integrity Is Preserved in Young, Healthy Men During a Single Bout of Strenuous Physical Exercise", Physiol. Res. 65: 281-291, 2016.
Mehendale, "Halogenated Hydrocarbons", 2010 Elsevier Ltd., 459-474.
Miller et al., "Oxidative Stress, Antioxidants, and Animal Function", 1993 J Dairy Sci 76:2812-2823.
Miner "The Glomerular Basement Membrane", Exp Cell Res. May 15, 2012; 318(9): 973-978.
Morgan et al., "Interaction of Maleic Acid With Thiol Compounds", Biochemical Laboratory, Cambridge, 1938, pp. 733-742.
Musante et al., "Active Focal Segmental Glomerulosclerosis Is Associated with Massive Oxidation of Plasma Albumin", J Am Soc Nephrol 18: 799-810, 2007.
Padberg et al., "Damage of the endothelial glycocalyx in chronic kidney disease", Atherosclerosis 234 (2014) 335e343.
Rahbar et al., "Endothelial glycocalyx shedding and vascular permeability in severely injured trauma patients", Journal of Translational Medicine (2015) 13.

(56) References Cited

OTHER PUBLICATIONS

Rasheed et al., "Reactive oxygen species damaged human serum albumin in patients with hepatocellular carcinoma", J. Exp. Clin. Cancer Res. 26,3, 2007.
Ravnskov et al., "Proteinuria in Pigs wiht Experimentally Induced Renal Damage", Contr. Neprol., vol. 1, pp. 50-61, 1975.
Reitsma et al., "The endothelial glycocalyx: composition, functions, and visualization", Eur J Physiol (2007) 454:345-359.
Riddick, "Control of Colloid Stability through Zeta Potential", book, vol. 1, Chapter 22, 1968.
Salmon et al., "Endothelial glycocalyx dysfunction in disease: albuminuria and increased microvascular permeability", J Pathol 2012; 226: 562-574.
Song et al., "Sodium fluoride induces nephrotoxicity via oxidative stress-regulated mitochondrial SIRT3 signaling pathway", Scientific Reports, 7:672, 2017.
Van Den Berg et al., "The Endothelial Glycocalyx Protects Against Myocardial Edema", Circulation Research, AHA Journals, 2003.
Vlahu et al., "Damage of the Endothelial Glycocalyx in Dialysis Patients", J Am Soc Nephrol 23: 1900-1908, 2012.
Warner et al., "Erythrocyte Sedimentation Rate and Related Factors in End-Stage Renal Failure", Nephron 1991: 57: 248.
Zausig et al., "The impact of crystalloidal and colloidal infusion preparations on coronary vascular integrity, interstitial oedema and cardiac performance in isolated hearts", Critical Care 2013, 17:R203.
Zeng, "Endothelial glycocalyx as a critical signalling platform integrating the extracellular haemodynamic forces and chemical signalling", J. Cell. Mol. Med. vol. 21, No. 8, 2017 pp. 1457-1462.

| | | | Treatment | | | | | Baseline: No Treatment | | |
|---|---|---|---|---|---|---|---|---|---|---|
| Chemistry | | 10/22/18 | 10/01/18 | 9/4/18 11:24 AM | 8/20/18 1:14 PM | 7/30/18 16:56 AM | 7/23/18 1:00 PM | 7/16/18 3:30 PM | 7/2/18 2:53 PM | 6/18/18 10:12 AM |
| Urine Creatinine | mg/dL | 281.7 | 213.2 mg/dL | 433.0 | 290.8 | 155.8 | P 401.0 | w 320.8 | z 297.9 | 264.4 |
| Urine Protein | mg/dL | 64.1 | 84.1 mg/dL | 120.1 | 62.1 | 100.2 | 143.5 | 197.4 | ** 260.7 | 123.6 |
| Urine Protein Creatinine Ratio | | 0.2 | 0.4 | 0.3 | 0.2 | 0.6 | 0.4 | 0.6 | 0.9 | 0.5 |
| Urinalysis | | 10/22/18 | 10/01/18 1:12 PM | 9/4/18 11:24 AM | 8/20/18 1:14 PM | 7/30/18 10:56 AM | 7/23/18 1:09 PM | 7/16/18 3:30 PM | 7/2/18 2:53 PM | 6/18/18 10:32 AM |
| Collection | | FREE-CATCH | FREE-CATCH | FREE-CATCH | FREE-CATCH | FREE-CATCH | FREE-CATCH | FREE-CATCH | CYSTOCENT... | NOT GIVEN |
| Color | | YELLOW | YELLOW | DARK YELL... | DARK YELL... | DARK YELL... | DARK YELL... | DARK YELL... | YELLOW | YELLOW |
| Clarity | | HAZY | HAZY | CLOUDY | HAZY | HAZY | HAZY | HAZY | HAZY | HAZY |
| Specific Gravity | | 1.051 | 1.046 | 1.055 | 1.050 | 1.032 | 1.059 | 1.047 | 1.051 | 1.050 |
| pH | | 6.0 | 6.5 | 6.5 | 6.0 | 6.0 | 6.5 | 7.0 | 7.0 | 7.5 |
| Urine Protein | | 1+(100-200 mg/dL) | TRACE | <1+(100-200.. | NEGATIVE | 1+(100-200.. | 1+(100-200.. | 3+(300-500.. | 3+(300-500.. | 2+(200-300.. |
| Glucose | | NEGATIVE | NEGATIVE | NEGATIVE | NEGATIVE | NEGATIVE | NEGATIVE | NEGATIVE | NEGATIVE | NEGATIVE |
| Ketones | | NEGATIVE | NEGATIVE | NEGATIVE | NEGATIVE | NEGATIVE | NEGATIVE | NEGATIVE | NEGATIVE | NEGATIVE |
| Blood/ Hemoglobin | | NEGATIVE | NEGATIVE | NEGATIVE | NEGATIVE | 3+ | 1+ | 1+ | NEGATIVE | NEGATIVE |

*FIG. 20*

| Urinalysis | 10/22/18 | 10/01/18 1:12 PM | 9/4/18 11:24 AM | 8/20/18 1:14 PM | 7/30/18 10:56 AM | 7/23/18 1:09 PM | 7/16/18 3:30 PM | 7/2/18 2:53 PM | 6/18/18 10:32 AM |
|---|---|---|---|---|---|---|---|---|---|
| | ← Treatment | | | | | | Baseline: No Treatment | | |
| Bilirubin | NEGATIVE | NEGATIVE | NEGATIVE | NEGATIVE | NEGATIVE | NEGATIVE | NEGATIVE | NEGATIVE | NEGATIVE |
| Urobilinogen | NORMAL | NORMAL | NORMAL | NORMAL | NORMAL | NORMAL | NORMAL | NORMAL | NORMAL |
| White Blood Cells | 6-10 | 2-5 | 6-10 | 50-75 | 6-10 | 6-10 | 2-5 | 0-2 | 6-10 |
| Red Blood Cells | 0-2 | 2-5 | 0-2 | 2-5 | 50-75 | 20-30 | 15-20 | 0-2 | 2-5 |
| Bacteria | NONE SEEN | NONE SEEN | NONE SEEN | NONE SEEN | NONE SEEN | NONE SEEN | NONE SEEN | NONE SEEN | NONE SEEN |
| Epithelial Cells | RARE (0-1) | RARE (0-1) | RARE (0-1) | 1N | 1+(1-2)/HPF | 2+(3-5)/HPF | 4+(>10)/HPF | RARE (0-1) | NONE SEEN |
| Mucus | NONE SEEN | NONE SEEN | NONE SEEN | NONE SEEN | NONE SEEN | NONE SEEN | NONE SEEN | NONE SEEN | NONE SEEN |
| Casts | NONE SEEN | NONE SEEN | NONE SEEN | NONE SEEN | NONE SEEN | NONE SEEN | NONE SEEN | NONE SEEN | NONE SEEN |
| Crystals | NONE SEEN | NONE SEEN | OCCASIONA... | NONE SEEN | NONE SEEN | 2+ AMMONI... | NONE SEEN | NONE SEEN | 2+ AMMONI... |

FIG. 21

COMPOSITIONS AND METHODS FOR TREATING AND PREVENTING PROTEINURIA AND ENDOTHELIAL EROSION

PRIORITY CLAIM

This application claims priority to U.S. Provisional Patent Application No. 62/578,076 entitled "COMPOSITIONS AND METHODS FOR TREATING AND PREVENTING PROTEINURIA AND ENDOTHELIAL EROSION" filed on Oct. 27, 2017, all of which is incorporated by reference herein.

BACKGROUND OF THE INVENTION

1. Field of the Invention

The present disclosure generally relates to proteinuria, Endothelial Erosion (EE) and related metabolic, vascular and neurological comorbidities. More particularly, the disclosure generally relates to compositions and methods for treating and preventing proteinuria, Endothelial Erosion (EE) and related metabolic, vascular and neurological comorbidities.

2. Description of the Relevant Art

The glomerular capillary wall of a healthy kidney functions as a barrier to prevent plasma proteins from entering the urine, based on the size and electrical surface charge of the plasma proteins. The primary barrier for ultrafiltration of plasma in renal glomeruli comprises four layers (e.g., the endothelial surface layer (ESL) including the endothelial glycocalyx, a fenestrated endothelium, a glomerular basement membrane, and diaphragms located between the foot processes of the podocytes). If the glomerulus is intact and functioning properly, only trace amounts of albumin and other large plasma proteins escape into the glomerular filtrate. Defective glomerular filtration is a common condition associated with a large number of acquired and inherited diseases. Defective glomerular filtration may result in the leakage, to varying degrees, of plasma albumin and other large plasma proteins, leading to protein in the urine (proteinuria), an insufficient quantity of essential plasma proteins in the bloodstream (hypoproteinemia), and progressive, degenerative kidney disease with many related metabolic, vascular and neurological comorbidities. Minimal Change Disease (MCD) is an example of a disease characterized by sudden and massive proteinuria and hypoproteinemia, as well as a rapid progression to End Stage Renal Disease (ESRD) with many related metabolic, vascular and neurological comorbidities (peripheral artery disease, peripheral neuropathy, retinopathy, systemic scarring, sclerosis, fibrosis, etc.).

Kidney disease is the ninth leading cause of death in the United States. It is estimated that over 31 million Americans (10% of the adult population) suffer from chronic kidney disease (CKD). However, most people with chronic kidney disease will not reach end stage renal disease (ESRD) because cardiac failure and/or some other cardiovascular related comorbidity (e.g. cardio-renal syndrome or renal-cardio syndrome) will kill them before the progression to ESRD can take place. There is a well-established clinical relationship between pathological states of the kidney and of the heart which displays the link between chronic kidney disease and cardiovascular disease; i.e., the severity of proteinuria can predict the rate of progression of cardiovascular disease as well as chronic kidney disease. One important determinant in a given person's rate of progression of chronic kidney disease and rate of progression of cardiovascular disease and related comorbidities is the amount of protein in the urine ("proteinuria") and the amount of protein in the serum (low albumin levels are referred to as "hypoalbuminemia," and hypoalbuminemia can be a better predictor of mortality rates in "otherwise healthy" subjects than even severe obesity). Generally, patients with greater amounts of proteinuria have a more aggressive form of chronic kidney disease as well as a more aggressive form of cardiovascular disease and related comorbidities tend to present with increased severity as well. For this reason, many researchers have attempted to design treatments to reduce and prevent the excess amounts of protein in urine. Amongst patients who have proteinuria, there is a broad range of excess protein that may be excreted. This range of excess protein loss through the urine can include small losses in conditions such as microalbuminuria (which is characterized by the excretion of 30-300 mg albumin in the urine during a 24-hour period) as well as larger losses, as seen in nephrotic syndrome (which is characterized by the excretion of over 3.5 g of protein in the urine during a 24-hour period) and any amount of protein excreted in the urine which falls in between these two conditions.

Accordingly, there exists a need, heretofore unfulfilled, for treatment methods that inhibit and/or ameliorate proteinuria.

SUMMARY

In some embodiments, a system and/or method may inhibit and/or ameliorate proteinuria and related comorbidities in a subject. In some embodiments, a system and/or method may inhibit and/or ameliorate Endothelial Erosion (EE) and related comorbidities in a subject. Proteinuria and/or Endothelial Erosion (EE) and related comorbidities may be inhibited and/or ameliorated by: maximizing a subject's serum zeta potential; repairing damage to the endothelial surface layer in a subject; making up for a subject's urinary losses of plasma proteins; and/or optimizing blood flow and facilitating healing of damage caused by Proteinuria and/or Endothelial Erosion (EE). A subject's serum zeta potential may be maximized by administering pharmaceutical compositions which: optimize the negative electrical surface charges of a subject's blood cells, plasma proteins, and/or endothelial surface layer; optimize the composition of a subject's bloodstream (e.g., ionic strength and ion concentrations), and/or optimize the properties of the subject's bloodstream (e.g., serum pH). In some embodiments, proteinuria and/or Endothelial Erosion (EE) and related comorbidities may be inhibited and/or ameliorated by administering pharmaceutical compositions which inhibit and/or ameliorate (e.g., maintain, repair and/or regrow the glycocalyx) damage to the endothelial surface layer in a subject. Proteinuria and/or Endothelial Erosion (EE) and related comorbidities may be inhibited and/or ameliorated by administering pharmaceutical compositions which increase blood flow, supply essential elements and/or replenish essential elements lost through proteinuria.

In some embodiments, a method may include treating proteinuria. The method may include adjusting a subject's serum zeta potential. The method may include increasing the health of a subject's endothelial surface layer. The method may include replenishing a subject's urinary losses of plasma proteins. The method may include ameliorating damage to a subject's glomerulus.

In some embodiments, the subject's serum zeta potential is a potential for a subject's blood cells, plasma proteins, and endothelial surface layer to electrostatically repel one another.

In some embodiments, adjusting a subject's serum zeta potential includes increasing the subject's serum zeta potential. Adjusting a subject's serum zeta potential may include maximizing the subject's serum zeta potential. Adjusting a subject's serum zeta potential may include electrostatically inhibiting coagulation in the subject's blood serum. Adjusting a subject's serum zeta potential may include administering a composition to the subject comprising sodium chloride, potassium chloride, magnesium chloride, potassium citrate, and/or olive leaf extract. Adjusting a subject's serum zeta potential may include adjusting a pH of the subject's serum. Adjusting a subject's serum zeta potential may include adjusting a pH of the subject's serum to between about 7.35 and about 7.45.

In some embodiments, increasing the health of subject's endothelial surface layer may include ameliorating damage to the endothelial surface layer. Increasing a health of subject's endothelial surface layer may include administering a composition to the subject which includes compounds used by the subject's own endothelial cells to form the subject's endothelial glycocalyx. Increasing the health of a subject's endothelial surface layer may include administering a composition to the subject which includes hyaluronic acid, N-acetyl glucosamine, glucosamine sulfate, chondroitin sulfate, n-acetyl cysteine, and/or methylsulfonylmethane.

In some embodiments, replenishing urinary losses of plasma proteins of the subject may include administering a composition to the subject which includes lactoferrin and sources of sodium, chloride, potassium, and magnesium.

In some embodiments, ameliorating damage to a subject's glomerulus may include administering a composition to the subject which includes tocotrienols, nattokinase, n-acetyl cysteine, and methylsulfonylmethane. Tocotrienols may include delta and gamma tocotrienols. Tocotrienols may include delta and gamma tocotrienols in a 90:10 ratio respectively. Damage to a subject's glomerulus may include scarring and/or sclerosis.

In some embodiments, a chemical composition may be configured to treat proteinuria. The composition may include a first group of compounds providing bioavailable sources of sodium, potassium, chloride, olive leaf extract, potassium citrate, and/or magnesium. The first group of compounds may adjust a subject's serum zeta potential. The composition may include a second group of compounds including hyaluronic acid, n-acetyl glucosamine, n-acetyl cysteine, methylsulfonylmethane, glucosamine sulfate and/or chondroitin sulfate. The second group of compounds may increase the health of a subject's endothelial surface layer. The composition may include a third group of compounds including bioavailable sources of magnesium, sodium, potassium, chloride, and/or lactoferrin. The third group of compounds may replenish a subject's urinary losses of plasma proteins. The composition may include a fourth group of compounds comprising nattokinase, methylsulfonylmethane, n-acetyl cysteine and/or tocotrienols. The fourth group of compounds may ameliorate damage to a subject's glomerulus.

In some embodiments, the first group of compounds provides bioavailable sources of sodium, potassium, chloride, olive leaf extract, potassium citrate, and magnesium.

In some embodiments, the second group of compounds includes hyaluronic acid, n-acetyl glucosamine, n-acetyl cysteine, methylsulfonylmethane, glucosamine sulfate and chondroitin sulfate.

In some embodiments, the third group of compounds may include bioavailable sources of magnesium, sodium, potassium, chloride, and lactoferrin.

In some embodiments, the fourth group may include nattokinase, methylsulfonylmethane, n-acetyl cysteine, and tocotrienols.

BRIEF DESCRIPTION OF THE DRAWINGS

Advantages of the present invention may become apparent to those skilled in the art with the benefit of the following detailed description of the preferred embodiments and upon reference to the accompanying drawings.

FIGS. 20-21 depict a spread sheet showing the preliminary results achieved by treating a cat with severe proteinuria with compositions described herein.

Figure 1D:
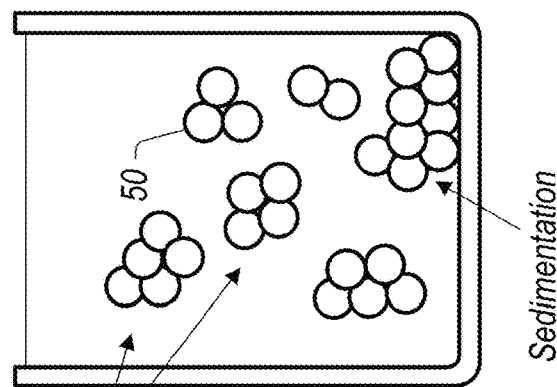
FIGS. 1A-D depicts a pictorial representation of zeta potential and the particles' ability in solution to electrostatically repel one another.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

The headings used herein are for organizational purposes only and are not meant to be used to limit the scope of the description. As used throughout this application, the word "may" is used in a permissive sense (i.e., meaning having the potential to), rather than the mandatory sense (i.e., meaning must). The words "include," "including," and "includes" indicate open-ended relationships and therefore mean including, but not limited to. Similarly, the words "have," "having," and "has" also indicated open-ended relationships, and thus mean having, but not limited to. The terms "first," "second," "third," and so forth as used herein are used as labels for nouns that they precede, and do not imply any type of ordering (e.g., spatial, temporal, logical, etc.) unless such an ordering is otherwise explicitly indicated. For example, a "third chemical compound added to a pharmaceutical composition" does not preclude scenarios in which a "fourth chemical compound added to a pharmaceutical composition" is added prior to the third chemical compound, unless otherwise specified. Similarly, a "second" feature does not require that a "first" feature be implemented prior to the "second" feature, unless otherwise specified.

Various components may be described as "configured to" perform a task or tasks. In such contexts, "configured to" is a broad recitation generally meaning "having structure that" performs the task or tasks during operation. As such, the component can be configured to perform the task even when the component is not currently performing that task. In some contexts, "configured to" may be a broad recitation of structure generally meaning "having chemical compounds that" perform the task or tasks during use. As such, the component can be configured to perform the task even when the component is not currently being used.

Various components may be described as performing a task or tasks, for convenience in the description. Such descriptions should be interpreted as including the phrase "configured to." Reciting a component that is configured to perform one or more tasks is expressly intended not to invoke 35 U.S.C. § 112, paragraph six, interpretation for that component.

The scope of the present disclosure includes any feature or combination of features disclosed herein (either explicitly or implicitly), or any generalization thereof, whether or not it mitigates any or all of the problems addressed herein. Accordingly, new claims may be formulated during prosecution of this application (or an application claiming priority thereto) to any such combination of features. In particular, with reference to the appended claims, features from dependent claims may be combined with those of the independent claims and features from respective independent claims may be combined in any appropriate manner and not merely in the specific combinations enumerated in the appended claims.

It is to be understood the present invention is not limited to particular devices or biological systems, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Thus, for example, reference to "a linker" includes one or more linkers.

DETAILED DESCRIPTION

Definitions

Unless defined otherwise, all technical and scientific terms used herein have the same meaning as commonly understood by one of ordinary skill in the art.

The terms "administration," "administering," or the like, as used herein when used in the context of providing a pharmaceutical, cosmeceutical or nutraceutical composition to a subject generally refers to providing to the subject one or more pharmaceutical, "over-the-counter" (OTC) or nutraceutical compositions in combination with an appropriate delivery vehicle by any means such that the administered compound achieves one or more of the intended biological effects for which the compound was administered. By way of non-limiting example, a composition may be administered via parenteral, subcutaneous, intravenous, intracoronary, rectal, intramuscular, intra-peritoneal, transdermal, or buccal routes of delivery. Alternatively, or concurrently, administration may be by the oral route. The dosage of pharmacologically active compound that is administered will be dependent upon multiple factors, such as the age, health, weight, and/or disease state of the recipient, concurrent treatments, if any, the frequency of treatment, and/or the nature and magnitude of the biological effect that is desired.

The term "ameliorating," as used herein, when used in the context of modulating a pathological or disease state, generally refers to reducing or treating damage resulting from the disease state. In some contexts, the term may generally refer to addressing in a positive manner one or more root causes of a disease state.

The term "animal" as used herein generally refers to any member of the kingdom Animalia, comprising multicellular organisms that have a well-defined shape and usually limited growth, can move voluntarily, actively acquire food and digest it internally, and have sensory and nervous systems that allow them to respond rapidly to stimuli: some classification schemes also include protozoa and certain other single-celled eukaryotes that have motility and animal like nutritional modes. Generally, the term animal as used herein does not refer to humans.

The term "anti-inflammatory" as used herein generally refers to a substance acting to reduce certain signs of inflammation (e.g., swelling, tenderness, fever, and pain).

The term "connected" as used herein generally refers to pieces which may be joined or linked together.

The term "coupled" as used herein generally refers to pieces which may be used operatively with each other, or joined or linked together, with or without one or more intervening members.

The term "directly" as used herein generally refers to one structure in physical contact with another structure, or, when used in reference to a procedure, means that one process effects another process or structure without the involvement of an intermediate step or component.

The terms "effective concentration" or "effective amount" as used herein generally refers to a sufficient amount of the pharmaceutically active agent that is added to decrease, prevent or inhibit or treat one or maladies described herein and/or related conditions. The amount will vary for each compound and upon known factors related to the item or use to which the pharmaceutically active agent is applied.

The terms "in need of treatment" or "in need thereof" when used in the context of a subject being administered a pharmacologically active composition, generally refers to a judgment made by an appropriate healthcare provider that an individual or animal requires or will benefit from a specified treatment or medical intervention. Such judgments may be made based on a variety of factors that are in the realm of expertise of healthcare providers, but include knowledge that the individual or animal is ill, will be ill, or is at risk of becoming ill, as the result of a condition that may be ameliorated or treated with the specified medical intervention.

The term "malady" as used herein generally refers to any disorder or disease of the body or any undesirable or disordered condition including, but not limited to, illness, sickness, affliction, complaint, ailment, indisposition, virus, disease, fungus, infection, disease, etc.

Terms such as "pharmaceutical composition," "pharmaceutical formulation," "pharmaceutical preparation," "nutraceutical," or the like, are used herein to generally refer to formulations that are adapted to deliver a prescribed dosage of one or more pharmacologically active compounds to a cell, a group of cells, an organ or tissue, an animal or a human. Methods of incorporating pharmacologically active compounds into pharmaceutical preparations are widely known in the art. The determination of an appropriate prescribed dosage of a pharmacologically active compound to include in a pharmaceutical composition in order to achieve a desired biological outcome is within the skill level of an ordinary practitioner of the art. A pharmaceutical composition may be provided as sustained-release or timed-release formulations. Such formulations may release a bolus of a compound from the formulation at a desired time, or may ensure that a relatively constant amount of the compound present in the dosage is released over a given period of time. Terms such as "sustained release," "controlled release," or "timed release" and the like are widely used in the pharmaceutical arts and are readily understood by a practitioner of ordinary skill in the art. Pharmaceutical preparations may be prepared as solids, semi-solids, gels, hydrogels, liquids, solutions, suspensions, emulsions, self-emulsifying agents, self-emulsifying drug delivery systems (SEDDS), aerosols, powders, or combinations thereof. Included in a pharmaceutical preparation may be one or more carriers, preservatives, flavorings, excipients, coatings, stabilizers, binders, solvents and/or auxiliaries that are, typically, pharmacologically inert. It will be readily appreciated by an ordinary practitioner of the art that, included within the meaning of the term are pharmaceutically acceptable salts of compounds. It will further be appreciated by an ordinary practitioner of the art that the term also encompasses those pharmaceutical compositions that contain an admixture of two or more pharmacologically active compounds, such compounds being administered, for example, as a combination therapy.

A "pharmaceutically or nutraceutically acceptable formulation," as used herein, generally refers to a non-toxic formulation containing a predetermined dosage of a pharmaceutical and/or nutraceutical composition, wherein the dosage of the pharmaceutical and/or nutraceutical composition is adequate to achieve a desired biological outcome. The meaning of the term may generally include an appropriate delivery vehicle that is suitable for properly delivering the pharmaceutical composition in order to achieve the desired biological outcome.

The term "pharmacologically inert," as used herein, generally refers to a compound, additive, binder, vehicle, and the like, that is substantially free of any pharmacologic or "drug-like" activity.

The terms "reducing" and "inhibiting," as used herein, when used in the context of modulating a pathological or disease state, generally refers to the prevention and/or reduction of at least a portion of the negative consequences of the disease state. When used in the context of an adverse side effect associated with the administration of a drug to a subject, the term(s) generally refer to a net reduction in the severity or seriousness of said adverse side effects.

The term "subject" as used herein generally refers to a mammal (e.g., felines, canines), and in particular to a human.

The term "colloid" as used herein generally refers to a mixture in which one substance of dispersed insoluble particles is suspended throughout a solution (e.g., blood is a colloid).

The term "plasma" as used herein generally refers to a constituent of the blood of an animal or a subject which can be separated from the red blood cells and clotting factors present in the blood stream of a living animal or subject.

The term "serum" as used herein generally refers to the entirety of flowing blood within the vasculature of a living animal or subject.

The phrase "therapeutically effective amount" generally refers to an amount of a drug or pharmaceutical composition that will elicit at least one desired biological or physiological response of a cell, a tissue, a system, animal or human that is being sought by a researcher, veterinarian, physician or other caregiver.

The phrase "zeta potential" generally refers to a measurement of the ability or the potential of insoluble particles in a colloidal solution to electrostatically repel one another. This may be dependent on several factors including the negative electrical surface charge of the particles and various properties of the solution (e.g., the pH). The zeta potential may generally refer to the potential difference existing between the surface of insoluble particles in a colloidal solution. Zeta potential was initially discovered in 1879 by German scientist Hermann von Helmholtz, and was influential in Einstein's 1905 paper about Brownian motion. A direct measurement of the serum zeta potential of a living organism is not feasible at the present time because the measurement device will collapse the fluid during the measurement process, but this difficulty with direct measurement does not make it impossible to indirectly measure a subject's or an animal's serum zeta potential. Researchers commonly use zeta potential calculations to design self-emulsifying drug delivery systems (SEDDS) for use in animals and/or subjects. In the same way, researchers are able to use indirect measurements of serum zeta potential to quantify results and identify chemical steps to maximize, improve, or optimize the serum zeta potential of an animal or subject.

The term "serum zeta potential" refers to the ability or the potential for a subject's blood cells and plasma proteins to electrostatically repel one another, and the ability or the potential for the subject's endothelial surface layer to electrostatically repel the subject's blood cells and plasma proteins. A subject's serum zeta potential may be dependent on several factors including the negative electrical surface charges of the subject's endothelial surface layer, blood cells, and plasma proteins, as well as various properties of the subject's bloodstream (e.g., the blood serum pH). The serum zeta potential can be affected, modified, collapsed or enhanced by a large number of widely divergent phenomena, most notably including: serum volume, serum composition, environmental factors (e.g., infectious disease, the presence of toxins, the physiological state of the subject or animal which may be active or at rest, etc.).

The term "Van der Waals Forces" refers to the tendency of insoluble particles in a solution to clump together and settle at the bottom of the container. In situations where a subject or animal's serum zeta potential suddenly collapses, environmental factors are said to have enabled the Van der Waals Forces to overcome the serum zeta potential, resulting in a loss of the ability of the negatively electrically charged components (e.g., plasma proteins, blood cells, and/or endothelial surface layer, etc.) of the subject or animal's serum to repel one another.

The phrase "maximize serum zeta potential" refers to a process in which a subject or animal is treated with compositions of a pharmaceutical and/or nutraceutical nature. These compositions are designed to impact the viscosity, volume, composition, and negative electrical surface charge of the components of the serum of a subject or animal such that the Van der Waals Forces between these components of the serum are overcome by the zeta potential of the serum of a subject or animal. Proteinuria is currently the best available proximate biomarker by which to ascertain the level of a subject or animal's serum zeta potential because the normal function of the glomerulus is not possible when serum zeta potential is reduced. Events such as proteinuria after exercise or proteinuria in conjunction with hyperglycemia are direct evidence that the characteristics of the serum are as critical to the normal function of the glomerulus as the structural integrity of the glomerulus itself; hence to maximize the serum zeta potential is to enhance the aspects of the serum which allow for normal renal function and circulation of serum.

The phrase "endothelial surface layer (ESL)" refers to the region of the vasculature which enables selective endothelial boundary permeability. There are three main parts of the endothelial surface layer, and each of them undergoes consistent modification in normal, ordinary life for both animals and subjects. The three parts of the ESL consist of: the endothelial glycocalyx, which is a hair-like growth produced by the endothelial cells comprised of heparan sulfate, hyaluronic acid, proteoglycans and glycosaminoglycans; objects and particles which become attached to the endothelial glycocalyx such as albumin and metals in circulation; and the boundary region, which is produced by the negative electric surface charge of the endothelial glycocalyx and which provides the negative electric potential needed to prevent erythrocytes and other large, insoluble serum particles from directly coming into contact with the endothelial glycocalyx, which would result in erosion. Albumin is a common protein in the human serum (typical concentrations range from 3.5-5.0 g/dL) and it is commonly found attached to the endothelial glycocalyx, as this is a normal part of metabolism for a subject and/or an animal in which the albumin molecule is transcytosed through the endothelial boundary into the interstitial space. The ESL is therefore a dynamic part of the physiology of a subject or an animal which needs continuous maintenance at the cellular level to ensure the health of a subject or an animal.

The term "Zeta Shield" is intended as a trademark and generally refers to an electromagnetic shield that lines all healthy blood vessels and protects the subject's endothelial cells and their associated endothelial surface layer from hydraulic friction and Endothelial Erosion (EE). The strength of a subject's Zeta Shield is dependent on the subject's serum zeta potential as well as the health of the endothelial surface layer.

The term "Endothelial Erosion (EE)" is intended as a trademark and to generally refer herein to hydraulic friction which damages or wears away and erodes the endothelial barrier (which consists of the basement membrane, the endothelial cells, and the endothelial surface layer including the endothelial glycocalyx) and inhibits the proper functioning of the vascular endothelium.

Embodiments

In some embodiments, systems presented herein may allow for inhibition and/or amelioration of proteinuria. It has been accepted by many in the medical field that the kidneys are size selective porous filters and that proteinuria is a result of inflammation and/or a result of an auto-immune disorder. Proteinuria is thought to be a result of inflammation causing kidney tissue to expand, causing the glomerular endothelial fenestrations to become larger, and allowing plasma proteins to pass through.

However, endothelial cell fenestrations (60-80 nm) are larger than plasma proteins (the largest of which are 9-11 nm) and as such if the kidney was a simple size-selective filter then plasma proteins would flow through the fenestrations of healthy kidneys, resulting in constant proteinuria. The size-selective filter model of kidney function does not explain sudden onset proteinuria, sudden failure of kidney transplants, the elevated erythrocyte sedimentation rate or elevated blood pressure associated with proteinuria, or minimal change nephrotic syndrome.

What does explain the inconsistencies of a size-selective filter model for kidneys is the new electrokinetic model of kidney function which is emerging in the literature. This model postulates that the glomerulus is an electrostatic filter that charge-selectively separates uncharged waste products from the negatively charged red blood cells and plasma proteins such that proteinuria is avoided by an electromagnetic interaction which is continuous in healthy subjects. The glomerular endothelial cells produce an endothelial glycocalyx as part of their endothelial surface layer. These kidney membranes have a negative electrical surface charge and as such electrostatically repel charged particles in the blood such as plasma proteins and red blood cells. Waste is either uncharged or positively charged and passes through endothelial fenestrations to be expelled through the urinary tract. Proteinuria therefore occurs at least in part due to kidney membranes losing their ability or potential to electrostatically repel plasma proteins, allowing the proteins to pass through the kidneys and into the urinary tract.

Figure 1C:
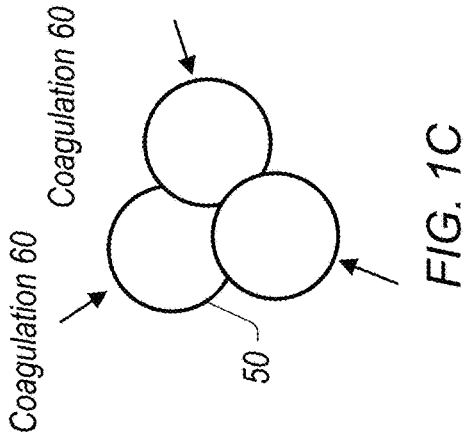
Figure 1B:
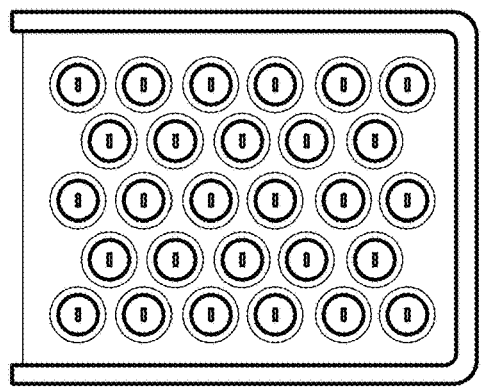
Figure 1A:
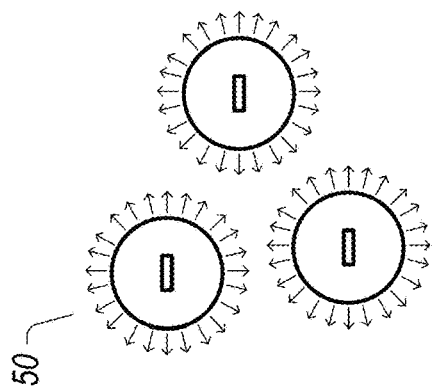

Further evidence can be seen for the electrokinetic model of kidney function when one looks at hypercoagulation in a subject's blood (erythrocyte sedimentation rate is a common test for hypercoagulation) that sometimes accompanies proteinuria. This hypercoagulation is the direct result of the loss of a subject's serum zeta potential, or the ability/potential for the subject's red blood cells and plasma proteins to electrostatically repel one another. FIGS. 1A-B depicts a pictorial representation of serum zeta potential and the particles' ability in solution to electrostatically repel one another. As is depicted in FIGS. 1A-B the particles 50 have an appropriate charge which allows the particles to repel one another in solution and therefore remain dispersed and resist coagulation. As is depicted in FIGS. 1C-D the particles 50 do not have an appropriate charge which allows the particles to repel one another in solution and therefore the particles begin to clump together and coagulate 60.

When there is a high zeta potential in a colloidal solution, particles distribute evenly over time throughout the solution due to the particles electrostatically repelling each other (e.g., see FIGS. 1A-B). When there is a low zeta potential in a colloidal solution, particles will clump together and settle to the bottom of the solution due to the activity of Van Der Waal's Forces which push the particles together (e.g., see FIGS. 1C-D). Zeta potential may be dependent on the negative electrical surface charge of the particles as well as various properties of the solution itself (e.g., pH, composition, viscosity, environment, etc.). The endothelial barrier has a negative electrical surface charge which allows for even fluid flow of the blood throughout the circulatory system by repulsing negatively charged blood cells and plasma proteins (e.g., reducing hydraulic friction, reducing blood pressure and reducing wear against the endothelial barrier such that subjects with a high serum zeta potential effectively have blood flow with minimal friction).

Figure 2:
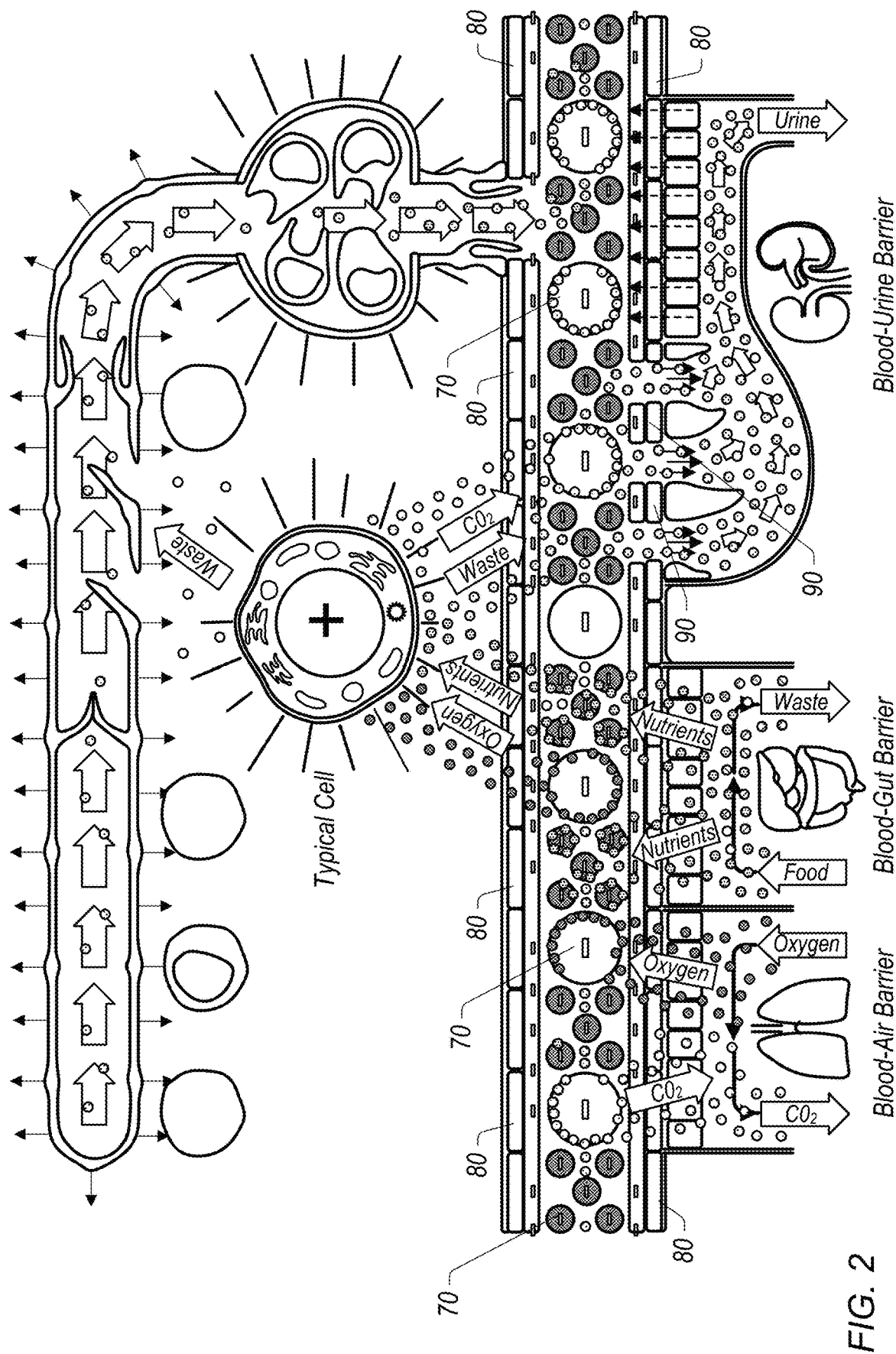
FIG. 2 depicts an embodiment of a portion of a subject's healthy and properly functioning cardiovascular system coupled to a healthy kidney with a healthy Zeta Shield (a healthy glycocalyx and a healthy zeta potential) with no Proteinuria and no Endothelial Erosion.

The vascular endothelium lining the inner surface of blood vessels serves as an interface for circulating blood components to interact with cells of the vascular wall and surrounding extravascular tissues. A function of vascular endothelia, especially those in exchange microvessels (capillaries and postcapillary venules), is to provide a semipermeable barrier that controls blood-tissue exchange of fluids, nutrients, and metabolic wastes while at the same time preventing pathogens or harmful materials in circulation from entering into tissues. Plasma leakage due to disruption and/or damage of vascular endothelia disturbs fluid homeostasis and impairs tissue oxygenation, a pathophysiological process contributing to multiple organ dysfunction associated with trauma, infection, metabolic disorder, and other forms of disease. FIG. 2 depicts an embodiment of a portion of a healthy subject's cardiovascular system coupled to a healthy kidney with a healthy Zeta Shield (a healthy glycocalyx and a healthy zeta potential) and how a subject's systems are supposed to function when healthy. Healthy red blood cells and plasma proteins (70) have a negative electrical surface charge which allows them to electrostatically repel one another and disperse evenly throughout an organism's bloodstream. A healthy endothelial barrier (80) also has a negative electrical charge which allows it to electrostatically repel red blood cells and plasma proteins; this process thus reduces hydraulic friction, blood pressure and wear against the endothelial surface layer. A healthy glomerular filtration barrier (GFB) (90) also has a negative electrical charge so it electrostatically repels red blood cells and plasma proteins, thereby electrostatically separating the waste in a subject's bloodstream from the negatively charged red blood cells and plasma proteins.

Similarly, as a subject's Zeta potential is reduced, several adverse effects result. Red blood cells begin to clump together and are no longer electrostatically repelled by the endothelial barrier resulting in increasing hydraulic friction, blood pressure, and wear against the endothelial barrier ("Endothelial Erosion"). Endothelial Erosion (EE) results from constant hydraulic friction and wear against the endothelial bather beginning with erosion of the endothelial surface layer. Endothelial Erosion (EE) can eventually lead to endothelial barrier failure and breach. In the same manner, the kidney filter membranes lose their ability to electrostatically repel plasma proteins resulting in the proteins passing through the kidney filter membranes along with waste products ("Proteinuria").

Figure 3:
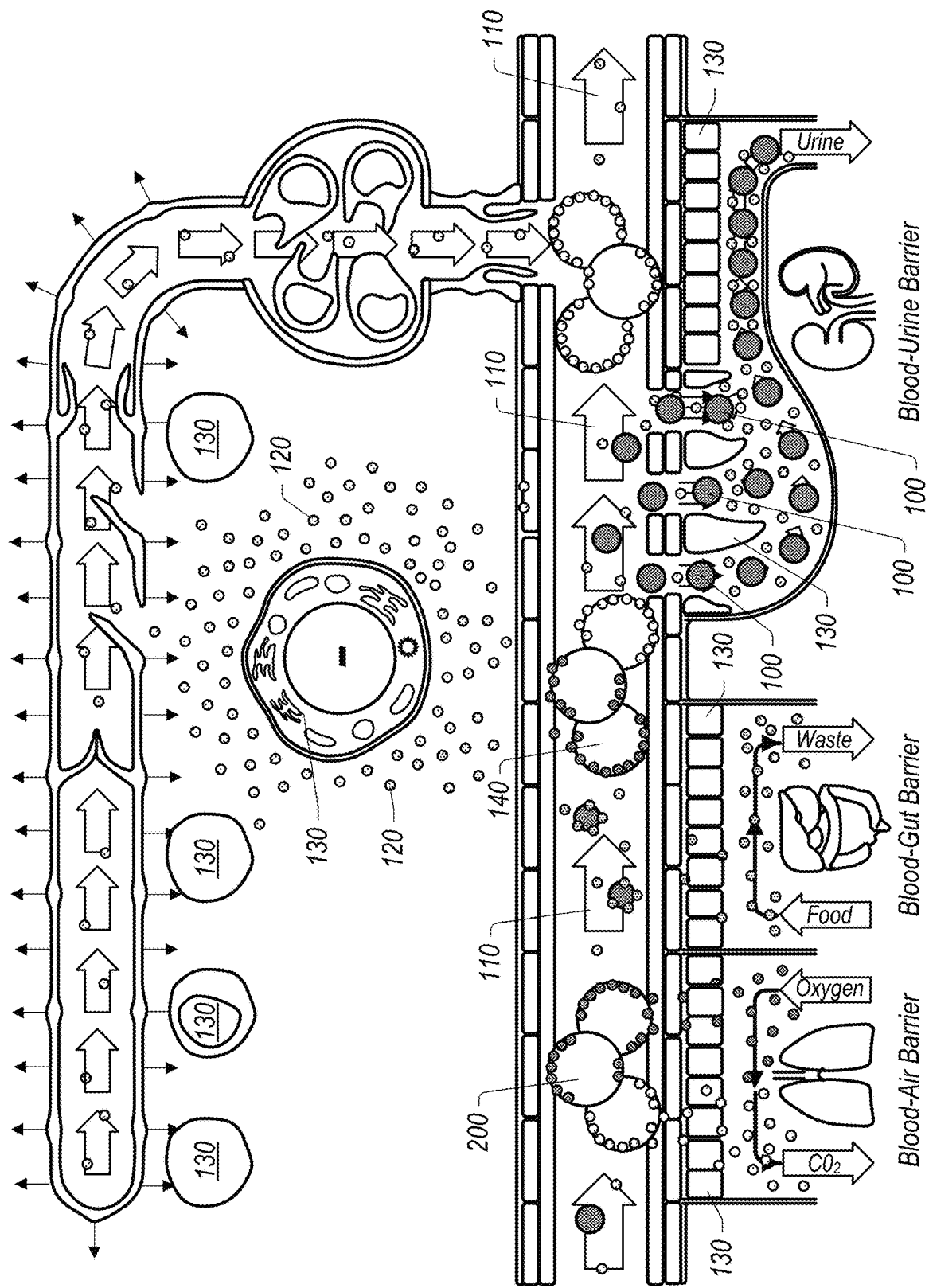
FIGS. 3-4 depict an embodiment of a portion of a subject's unhealthy cardiovascular system shortly after experiencing a sudden, massive loss of zeta potential as typically seen in Minimal Change Disease (MCD) and Pre-eclampsia. The loss of zeta potential causes Proteinuria, hypercoagulation and hypertension. The Proteinuria causes hypoproteinemia which leads to progressive systemic ischemia, edema, oxidative stress and iron deficiency anemia. At this initial stage, the subject's glycocalyx is still intact and there is no Endothelial Erosion.
Figure 4:
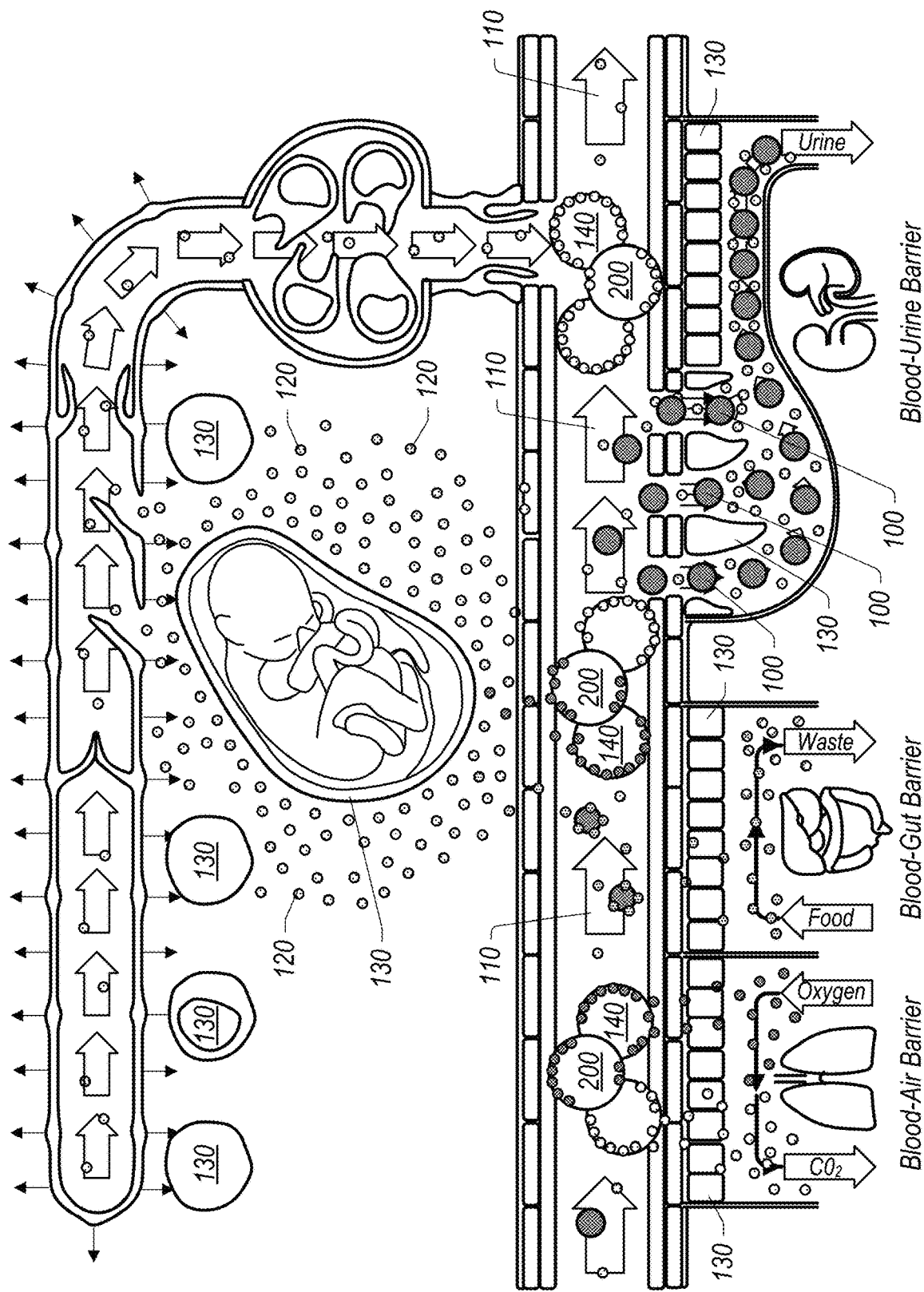
Figure 5:
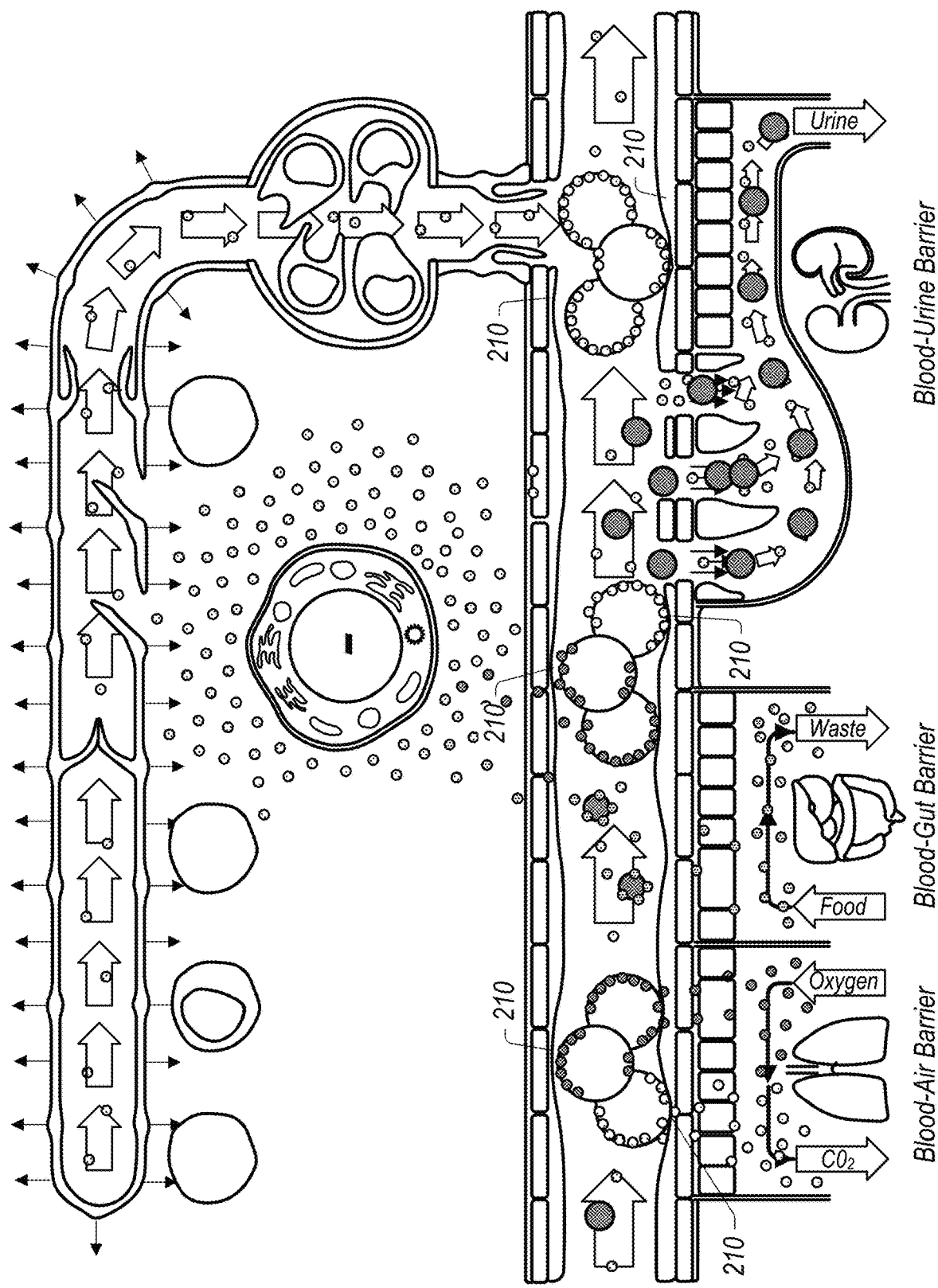
FIGS. 5-15 depict an embodiment of a portion of a subject's unhealthy cardiovascular system showing the progression of Endothelial Erosion caused by hydraulic friction due to the loss of the subject's Zeta Potential. Endothelial Erosion begins with the erosion of the glycocalyx (FIG. 4) and ends in catastrophic failure or thrombosis (FIG. 15) causing a heart attack, stroke or pulmonary embolism.
Figure 6:
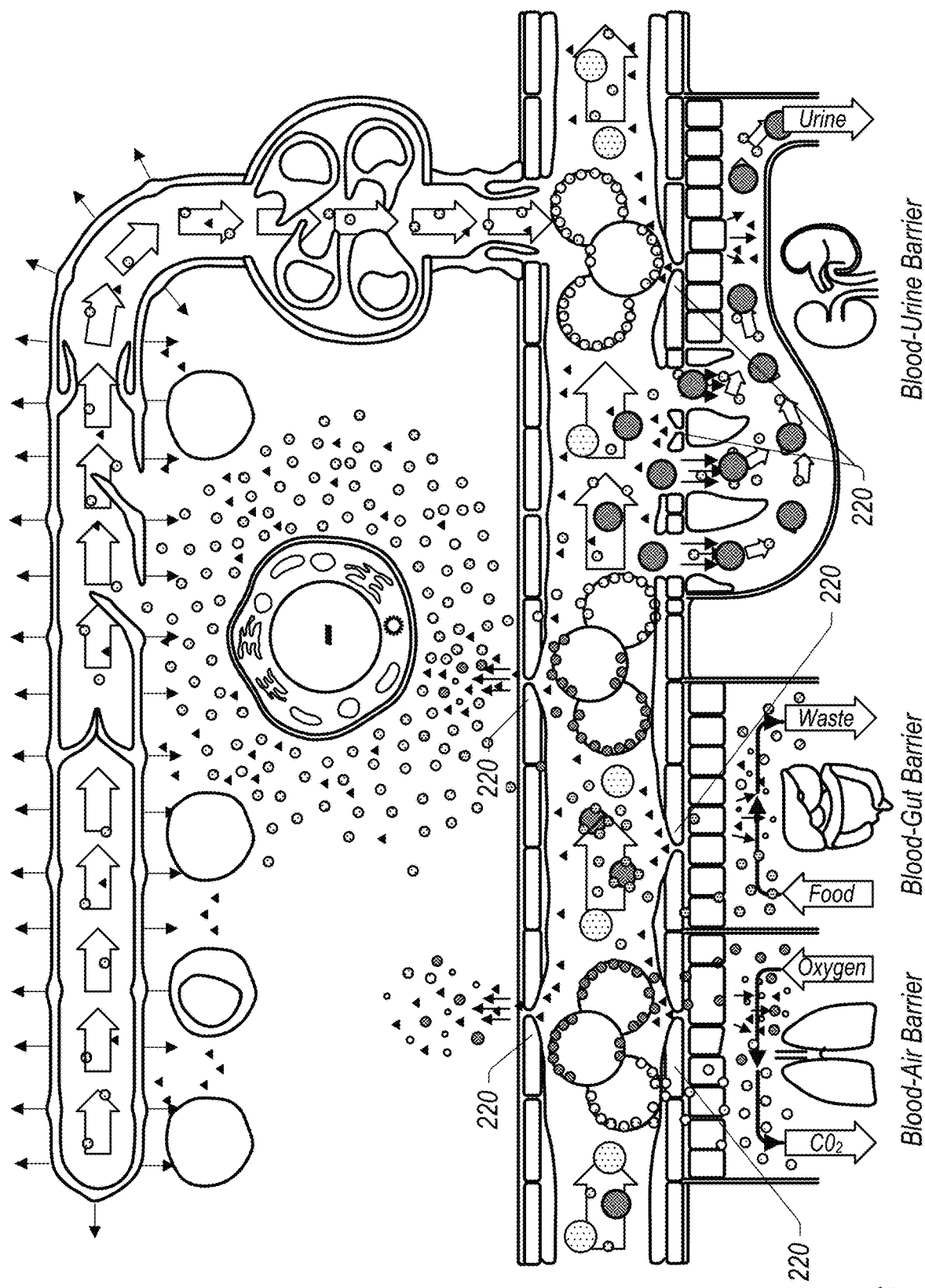
Figure 7:
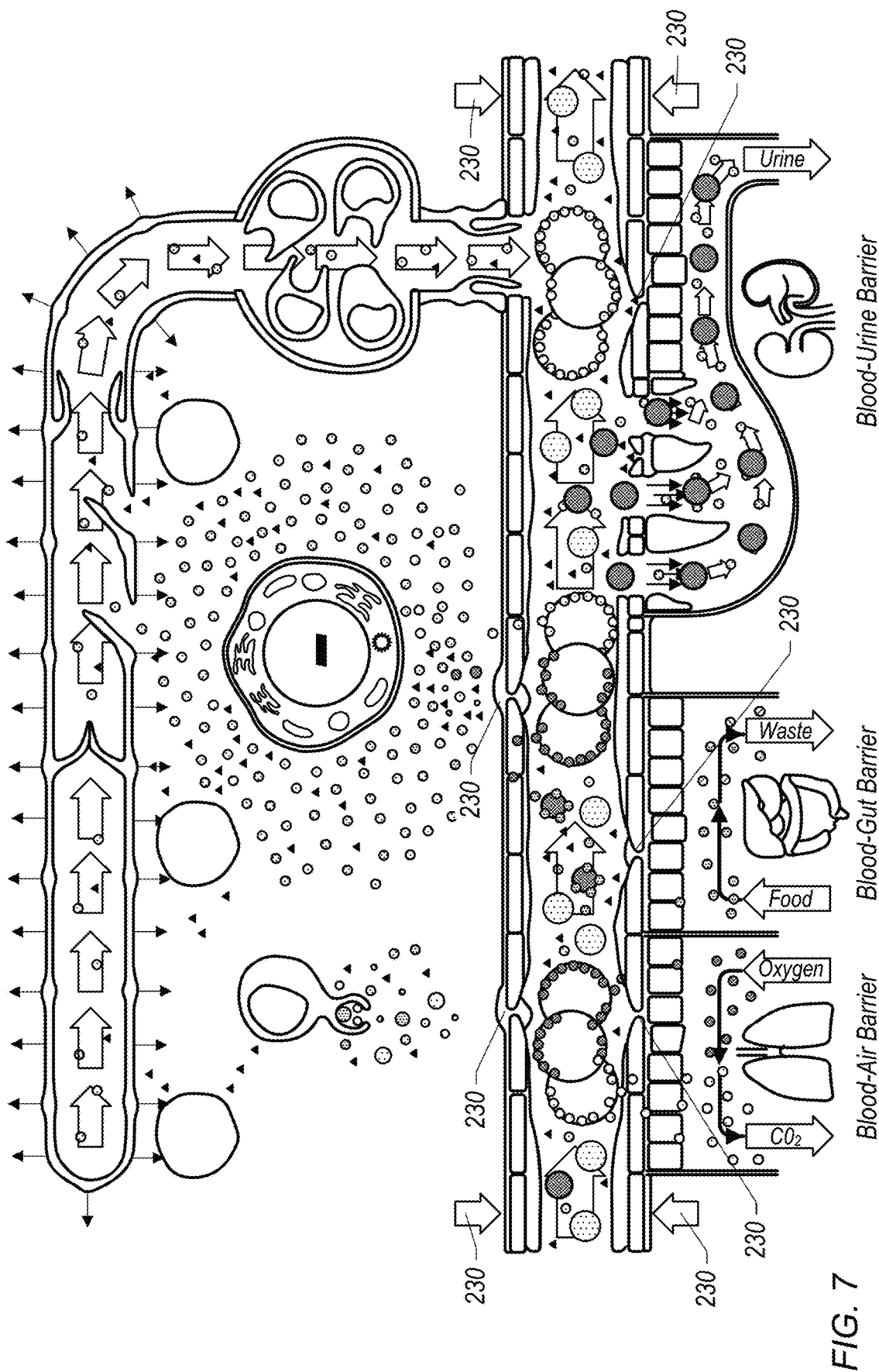
Figure 8:
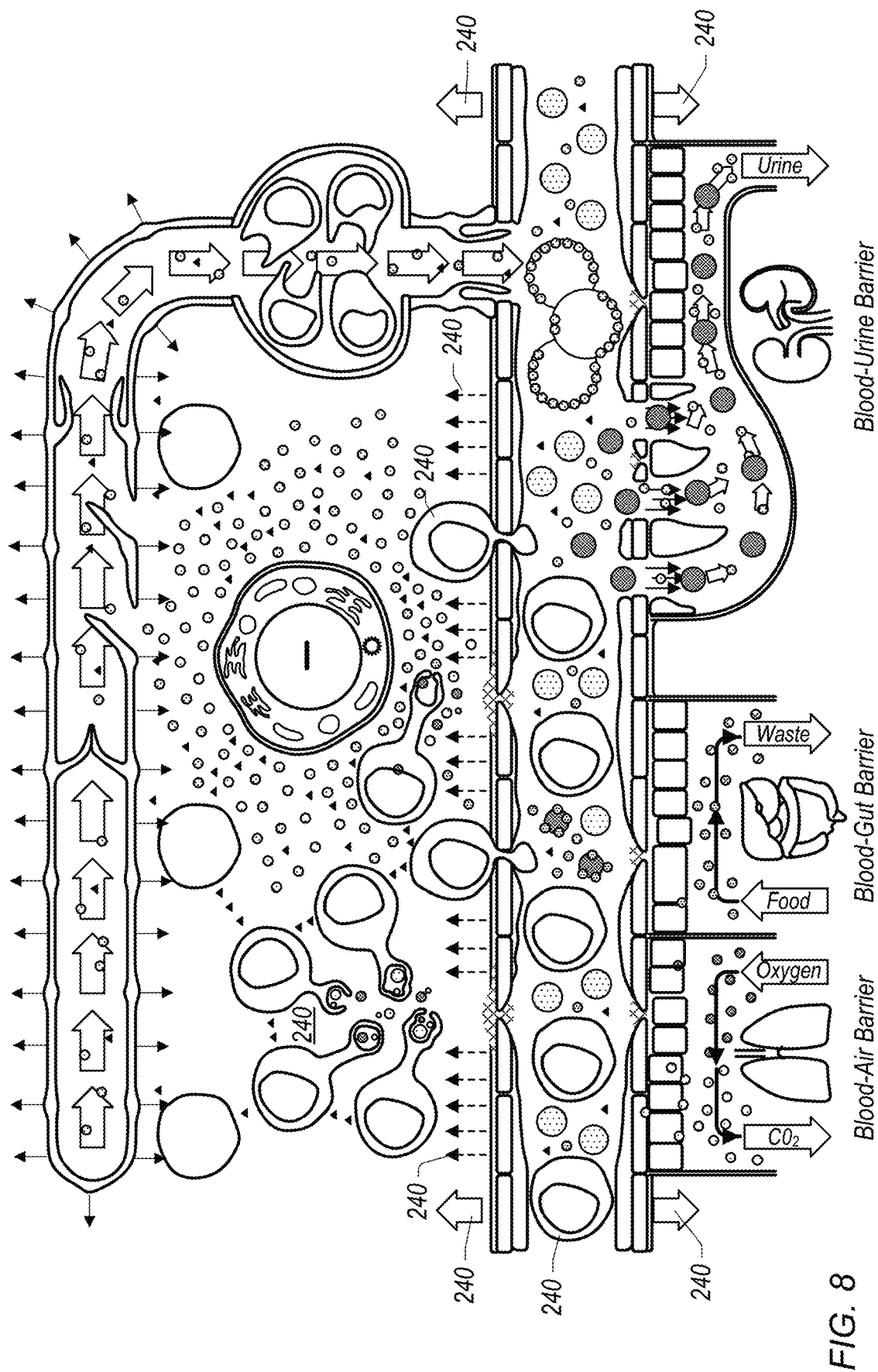
Figure 9:
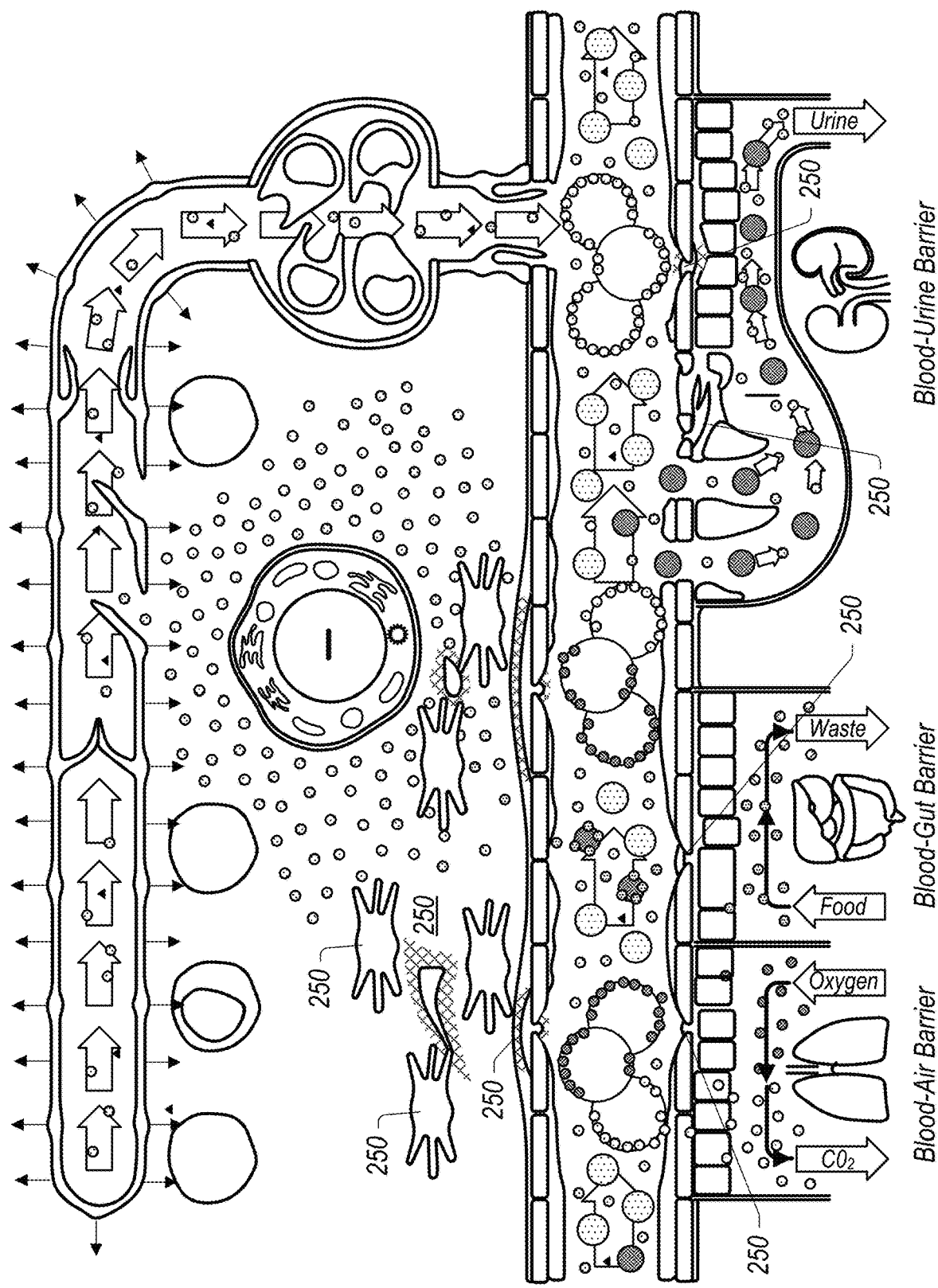
Figure 10:
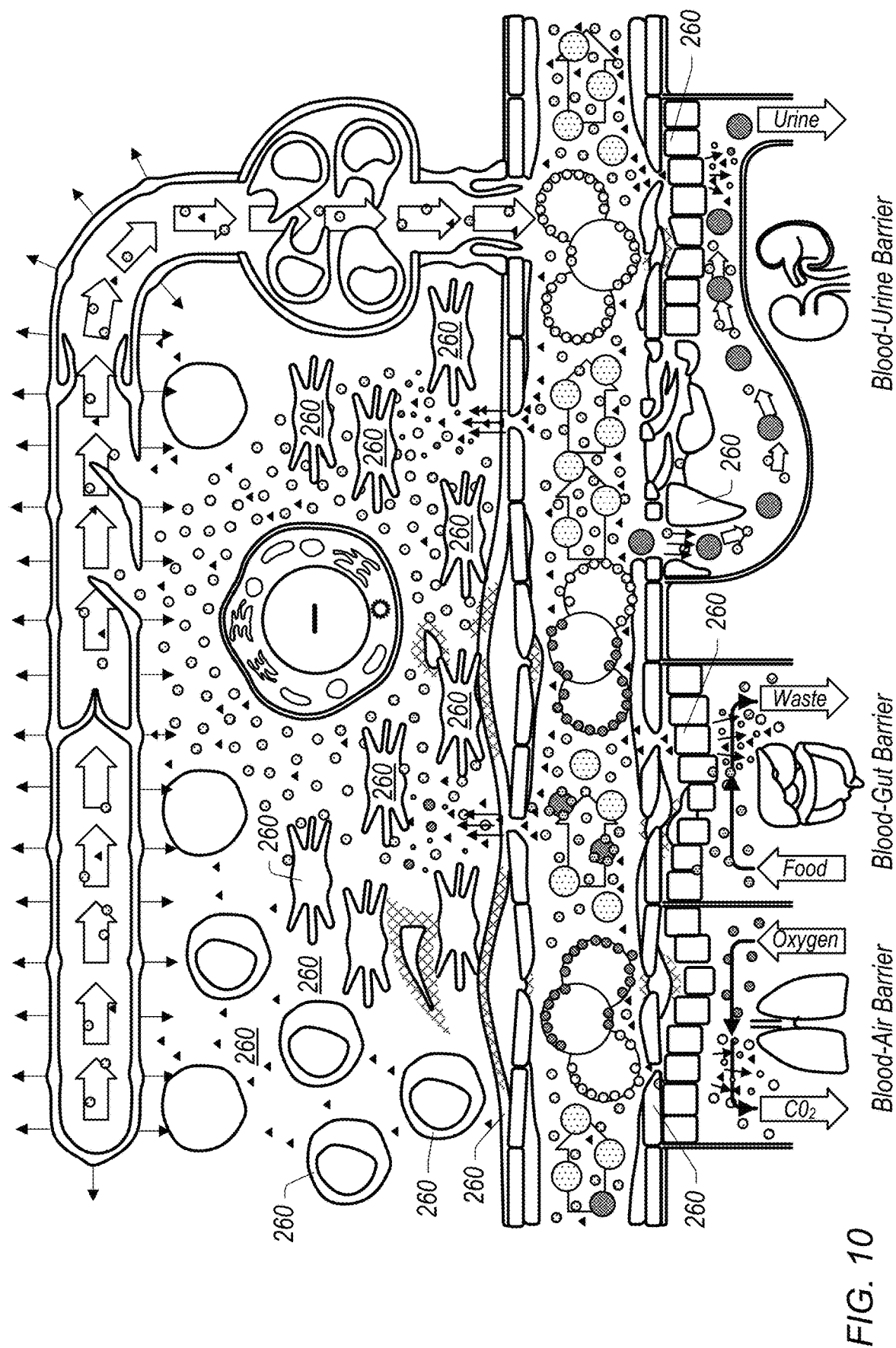
Figure 11:
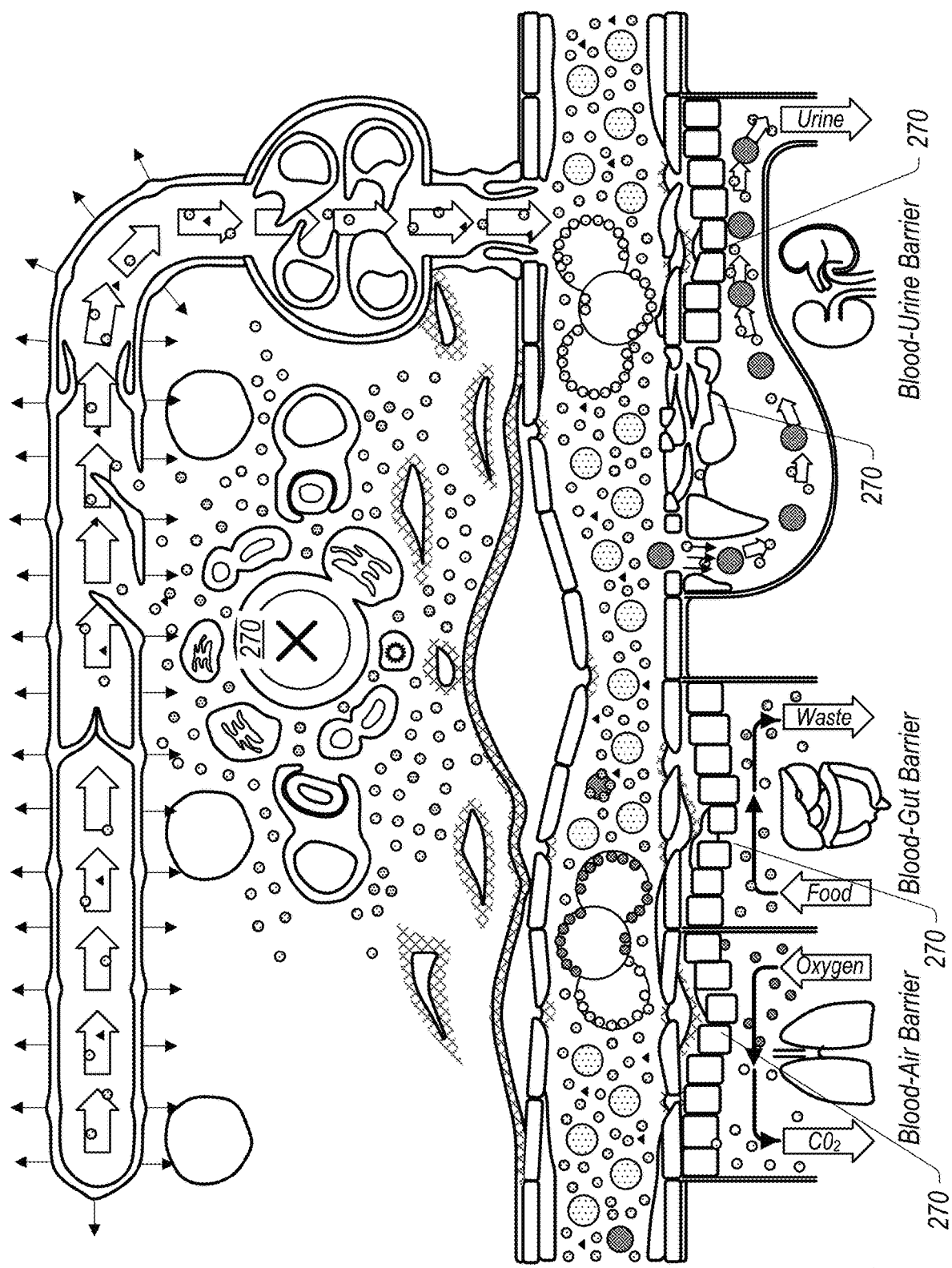
Figure 12:
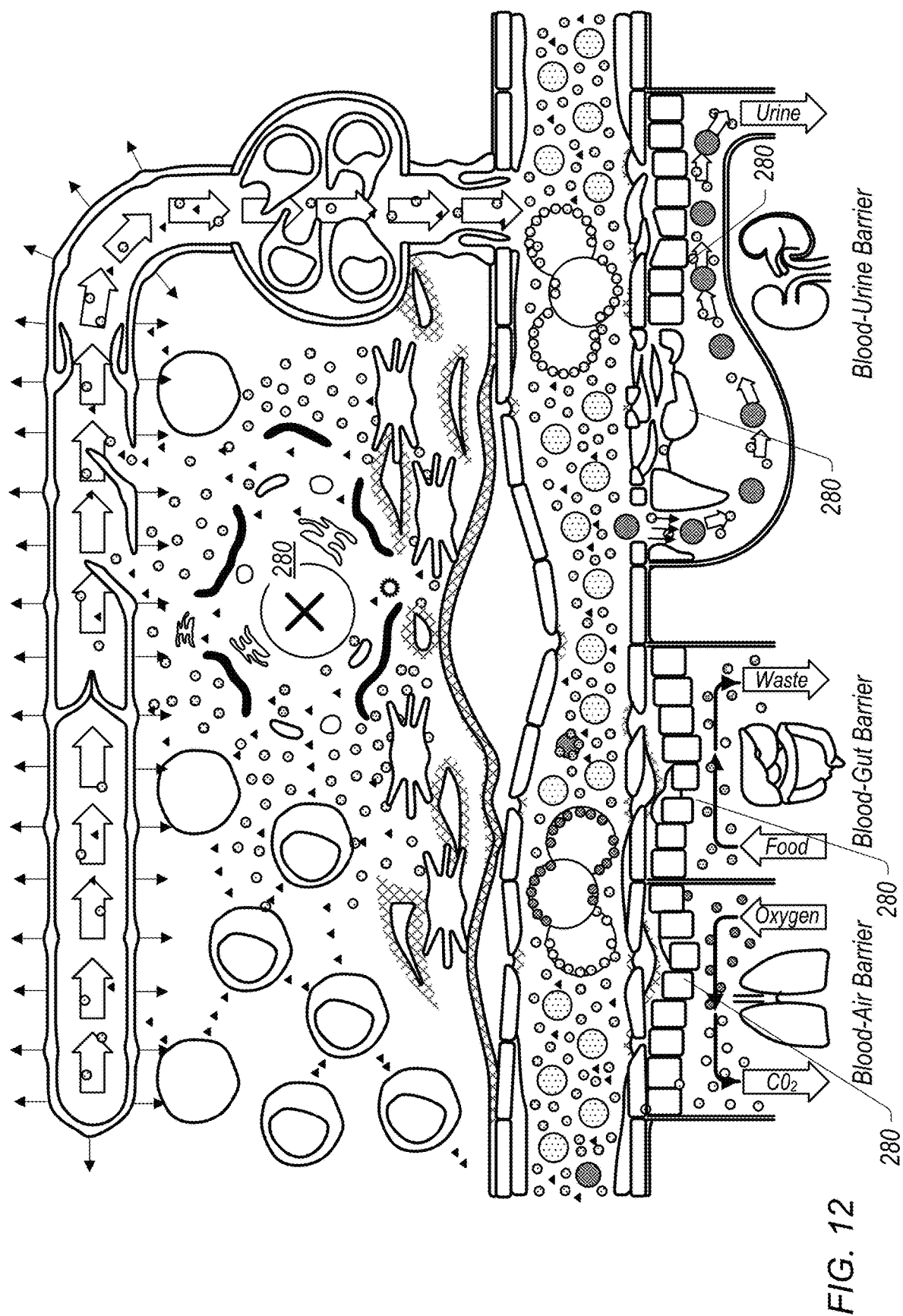
Figure 13:
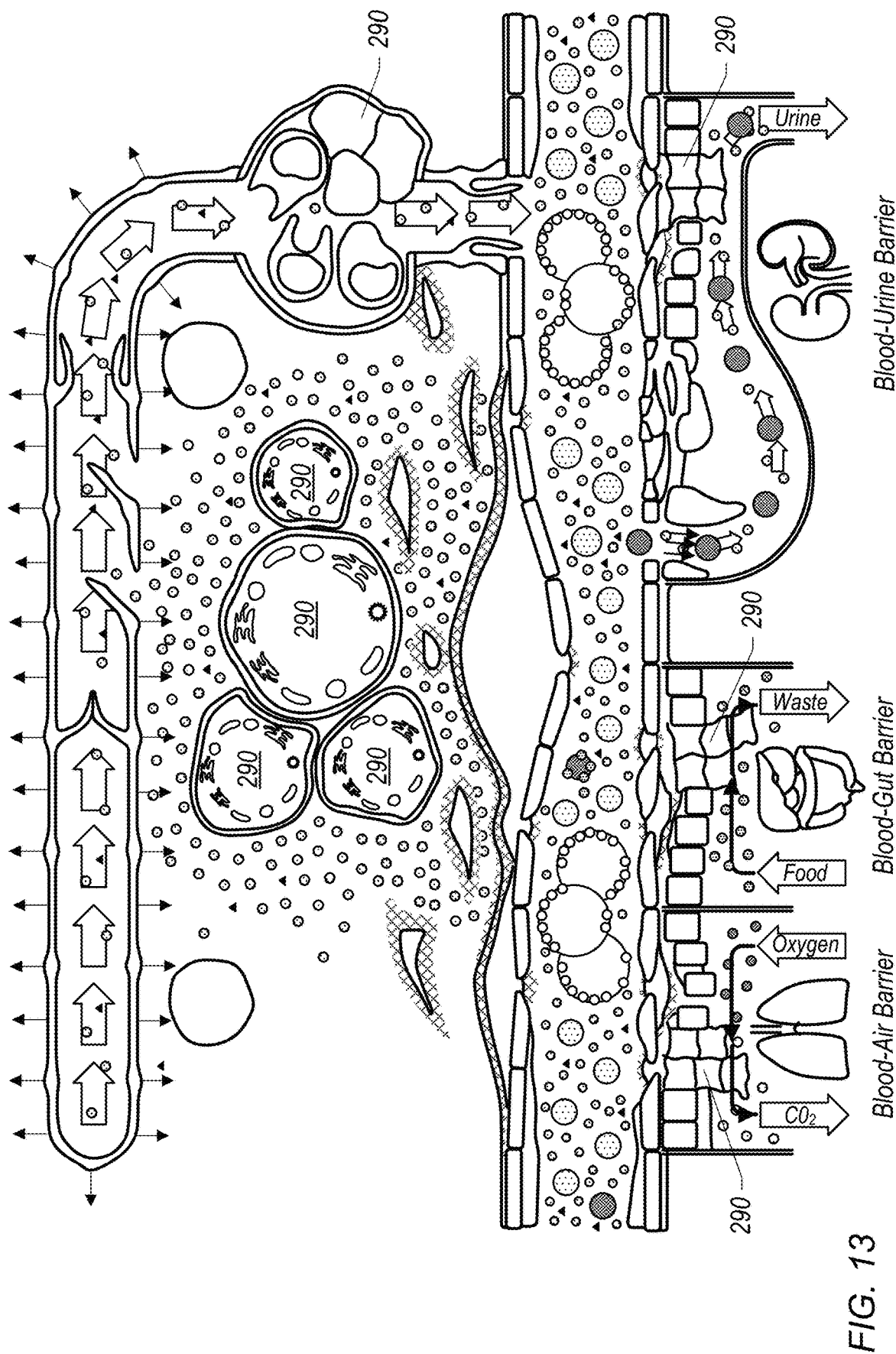
Figure 14:
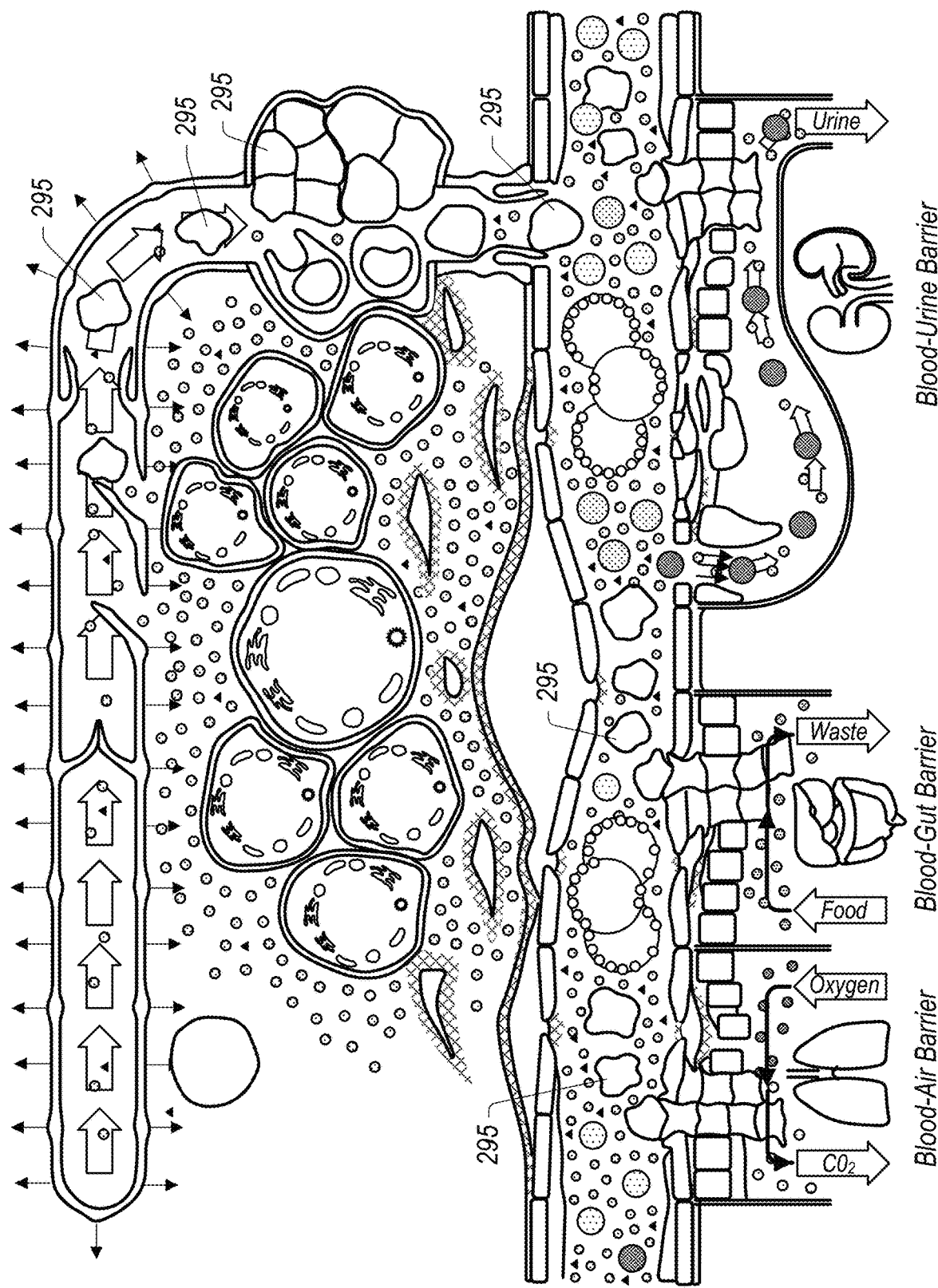
Figure 15:
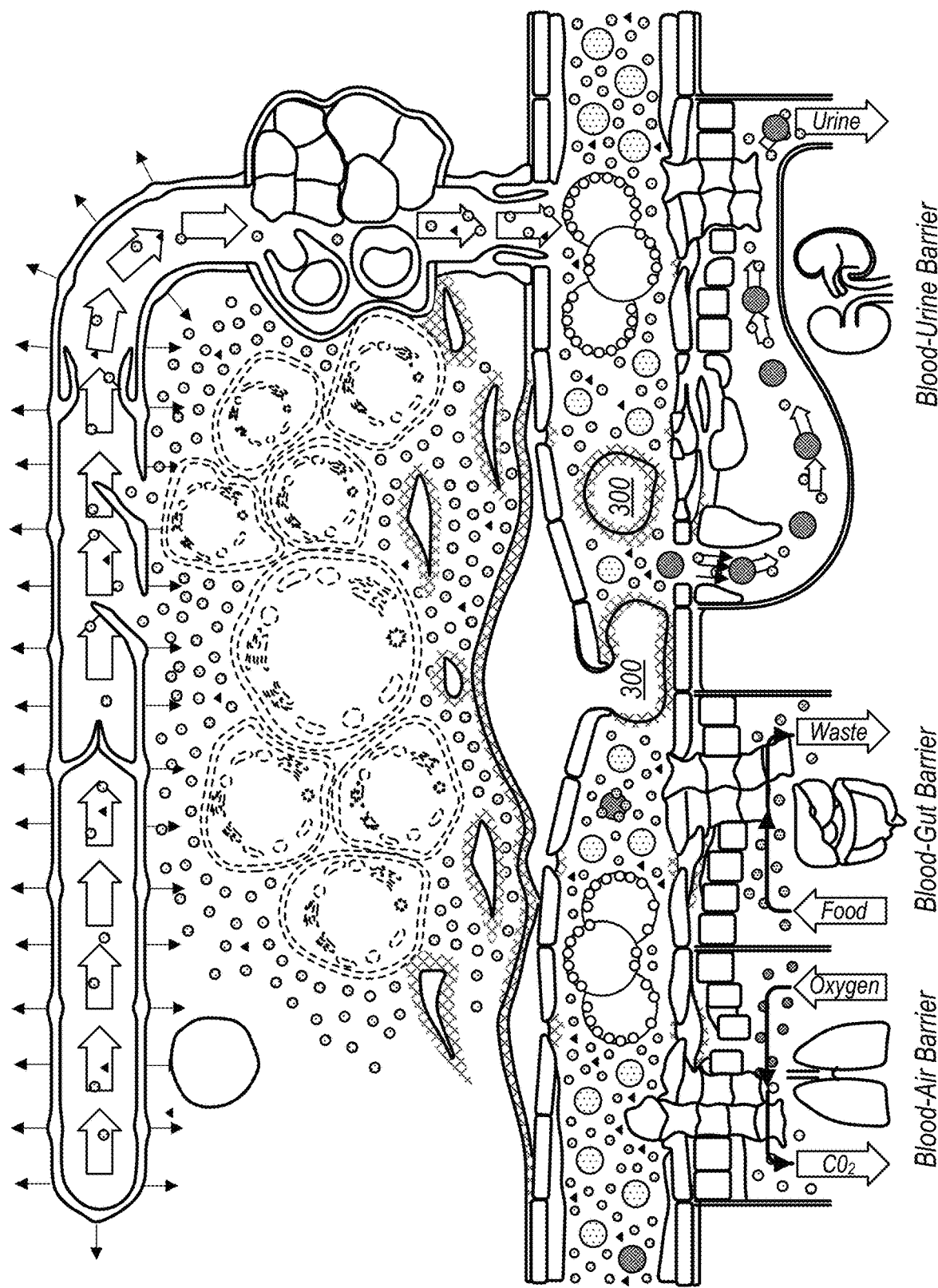

FIGS. 3-4 depict an embodiment of a portion of an unhealthy subject's cardiovascular system shortly after experiencing a sudden, massive loss of serum zeta potential as typically seen in Minimal Change Disease (MCD) and Pre-eclampsia. The loss of serum zeta potential causes Proteinuria 100, hypercoagulation and hypertension. Proteinuria leads to hypoproteinemia 110, a condition in which an insufficient quantity of plasma proteins remain to transport nutrients to cells or to pull the waste products from cells into the subject's bloodstream. If the hypoproteinemia continues unabated, cells throughout the subject will be stressed and can begin to die from toxicity and nutrient deficiency commonly referred to as ischemia 130. As hypoproteinemia continues, cellular waste continues to collect in the subject's tissues causing severe swelling or edema 120. Due to urinary losses of transferrin and ceruloplasmin, oxidative stress 140 and iron deficiency anemia 140 can result. One or more of these conditions may lead to the liver responding by overproducing cholesterol, a condition commonly referred to as hyperlipidemia.

Figure 16:
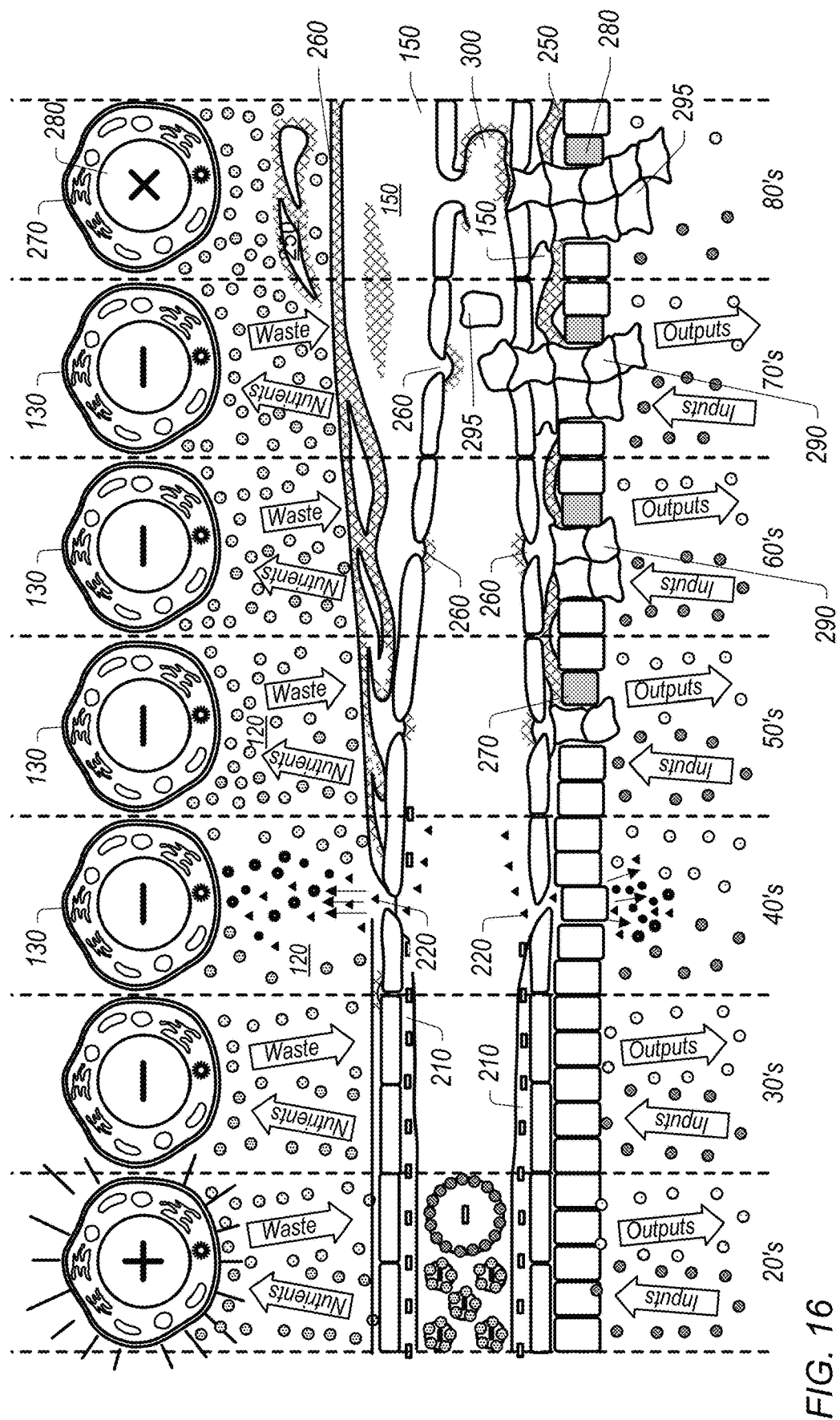
FIG. 16 depicts a pictorial summary of a theory of chronic degenerative disease over an average human lifespan.

FIGS. 5-15 depict an embodiment of a portion of an unhealthy subject's cardiovascular system with a depleted zeta potential and a second pathway leading to catastrophic failure of the subject's body's systems resulting from loss of the subject's serum zeta potential over an extended period of time. The second pathway typically extends over a period of decades and currently is thought to be normal conditions or ailments associated with aging. The second pathway may begin with red blood cells coagulating due to a loss of serum zeta potential. The coagulated blood cells rub against the endothelial barrier, increasing hydraulic friction, blood pressure, and wear of the endothelial barrier. The process begins with glycocalyx erosion 210 from the friction generated by clumps of coagulated blood cells penetrating into the endothelial surface layer, causing damage to the endothelial glycocalyx and damaging the endothelial cells (e.g., see FIG. 5). Glycocalyx erosion leads to Endothelial Erosion (EE), which includes endothelial cell damage and endothelial barrier breach 220 (e.g., see FIG. 6). Endothelial barrier breach typically results in a first immune response and vasoconstriction and hemostasis 230 (e.g., see FIG. 7). The second pathway continues on with a second immune response including vasodilation, inflammation and proliferation of white blood cells 240 (e.g., see FIG. 8). Typically, a third immune response follows the first two, consisting of a repair and remodeling process which produces scarring and fibrosis 250 (e.g., see FIG. 9). This vicious cycle of chronic insult and injury will continue on, if left unchecked, resulting in chronic degenerative diseases including chronic inflammation and chronic fibrosis 260 (e.g., see FIG. 10). The chronic degenerative disease results in ischemic cell death including apoptosis 270 (e.g., see FIG. 11) and necrosis 280 (e.g., see FIG. 12). Along with these conditions, the ischemic cell injury which results from the sustained cellular stress caused by the loss of a subject's serum zeta potential can lead to metabolic degeneration, epigenetic deregulation, and/or genetic mutation 290 (e.g., see FIG. 13). In some cases, the breakdown in a subject's cardiovascular system may lead to cancer and metastasis 295 (e.g., see FIG. 14). Ultimately, all of this damage can result in catastrophic failure of one or more major organ systems of the subject (e.g., cardiac arrest, stroke, pulmonary embolism) 300 (e.g., see FIG. 15). As mentioned loss of serum zeta potential can happen suddenly or slowly over decades. FIG. 16 depicts a pictorial summary of a theory of chronic degenerative disease over an average human lifespan.

Figure 18:
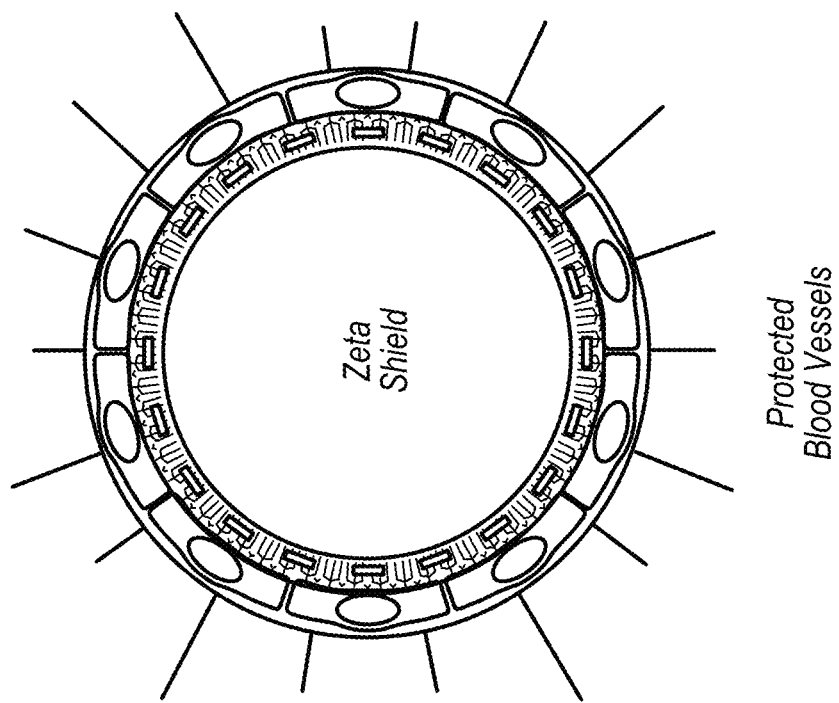
FIG. 18 depicts an embodiment of a cross-section of a subject's healthy blood vessel protected from hydraulic friction and Endothelial Erosion by a healthy Zeta Shield (a healthy glycocalyx and a healthy zeta potential strong enough to electrostatically repel blood cells and plasma proteins).
Figure 17:
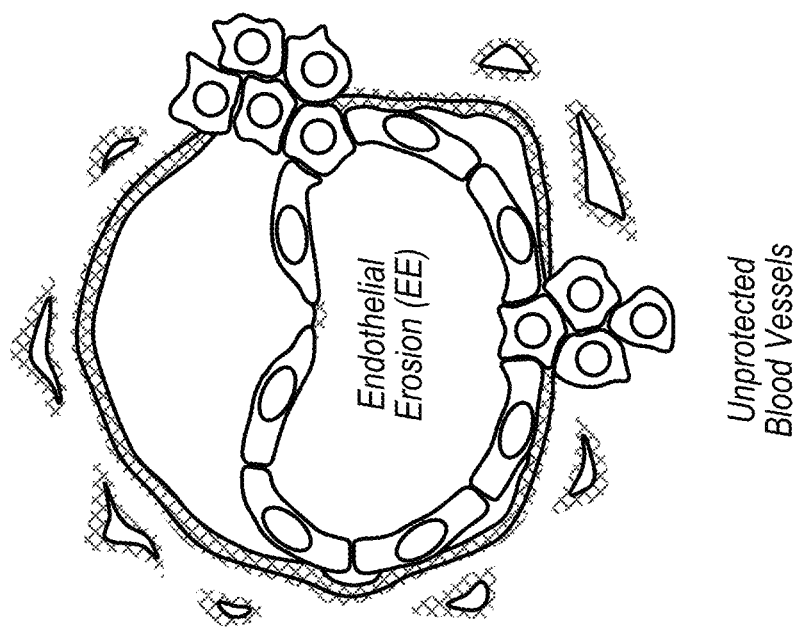
FIG. 17 depicts an embodiment of a cross-section of a subject's unhealthy blood vessel damaged by hydraulic friction and Endothelial Erosion due to the loss of the subject's Zeta Potential.

FIGS. 17-18 depict an embodiment of cross-section of a portion of an unhealthy subject's cardiovascular system and a healthy subject's cardiovascular system with a healthy Zeta Shield respectively.

Figure 19:
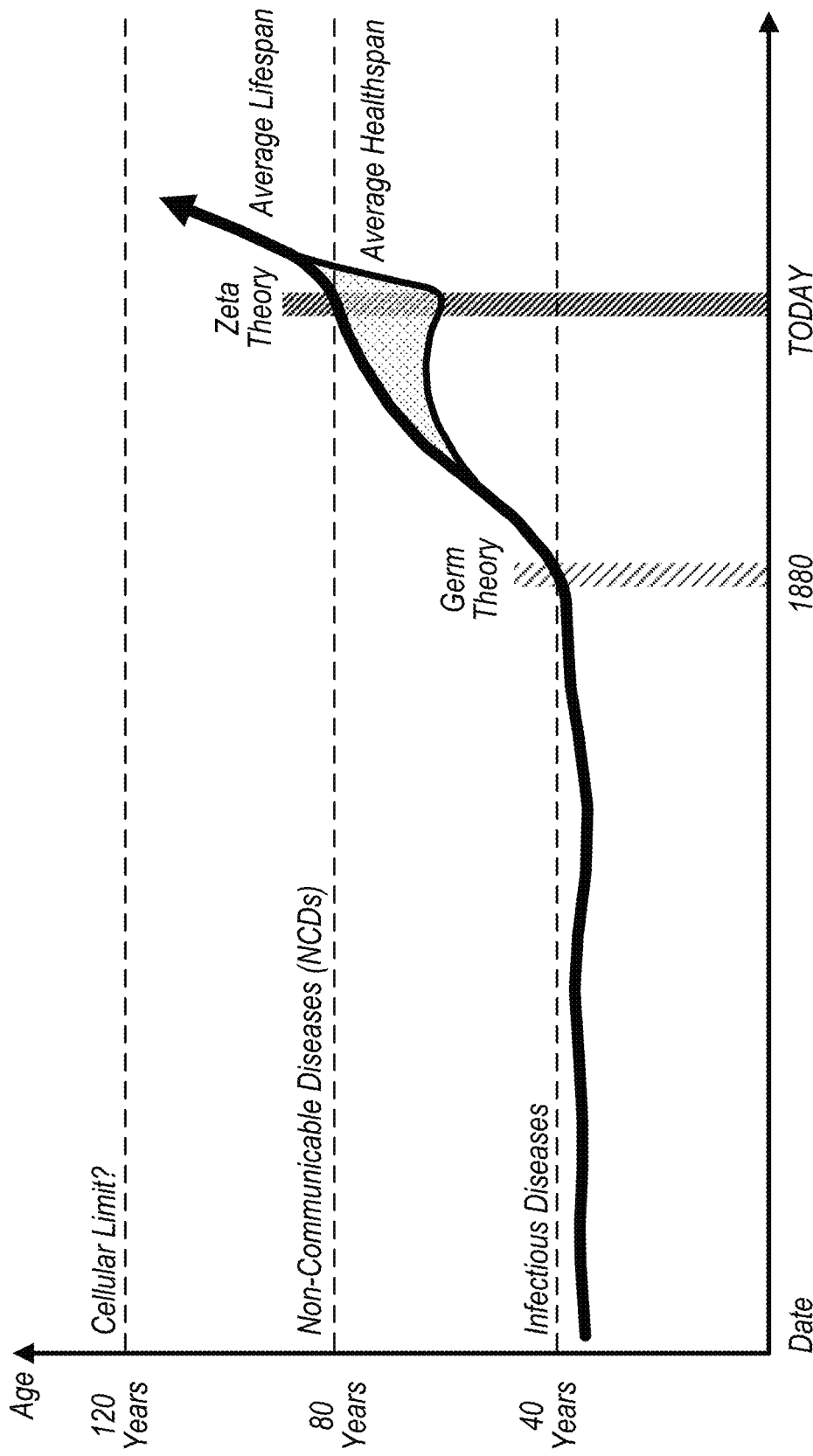
FIG. 19 depicts a graph of the average human lifespan for the at least the last several hundred years and how it has improved and could improve even more.

Loss of serum zeta potential leads to Endothelial Erosion (EE), which, when left untreated, eventually results in a variety of conditions as discussed herein (e.g., endothelial barrier failure, vasoconstriction, hypertension, hyperlipidemia, Chronic Inflammation, "Auto-Immune" response, scarring, sclerosis, fibrosis, amyloidosis, plaque build-up, etc.). Many of these diseases are associated with aging and accepted as normal. In some embodiments, many other diseases may be traced back to a loss of serum zeta potential and endothelial erosion. Many non-communicable diseases (NCDs) associated with aging may be traced back to a loss of serum zeta potential. NCDs may pose a greater threat to global economic development than fiscal crisis or infectious diseases. The lost output caused by the top five NCDs over the next two decades may exceed forty-seven trillion dollars. FIG. 19 depicts a graph of the average human lifespan for the at least the last several hundred years and how it has improved and could be improved even more. As can be seen in FIG. 19, once mankind understood how infectious diseases worked and how to prevent and/or treat infectious diseases in the late $19^{th}$ century, the average lifespan roughly doubled. If humanity manages to solve the problem of non-communicable diseases, the average lifespan of humans should increase greatly again. In some embodiments, such NCDs may include: chronic eye diseases (e.g., macular degeneration, retinopathy, cataracts, glaucoma); chronic skin diseases (e.g., systemic sclerosis (scleroderma), psoriasis, dermatitis, eczema, rosacea, lupus); chronic bone, joint, and muscle diseases (e.g., arthritis, osteoporosis, fibromyalgia, degenerative disc disease); chronic gastrointestinal diseases (e.g., irritable bowel syndrome, inflammatory bowel disease, Chron's disease, leaky gut syndrome, ulcerative colitis); chronic kidney diseases (e.g., nephritis, nephrosis, nephrotic syndrome, minimal change disease, focal segmental glomerular sclerosis, membranous nephropathy, end stage renal disease); diabetes and diabetes complications (e.g., prediabetes, type 1 and 2 diabetes, peripheral artery disease, peripheral neuropathy, retinopathy, end stage renal disease); chronic respiratory diseases (e.g., chronic obstructive pulmonary disease; interstitial lung disease, idiopathic pulmonary fibrosis, asthma, emphysema, bronchitis); cancer (e.g., lung, breast, colorectal, stomach, prostate, kidney, pancreatic, skin, lymphatic, cervical, liver, bladder); cardiovascular diseases (e.g., hypertension, atherosclerosis, heart attack, stroke, peripheral artery disease, erectile dysfunction, chronic fatigue syndrome, metabolic syndrome); pre-eclampsia and eclampsia; and/or chronic neurological diseases (e.g., dementia, Alzheimer's, Parkinson's, Autism, Epilepsy, multiple sclerosis, amyotrophic lateral sclerosis, peripheral neuropathy, depression, obsessive-compulsive disorder, attention deficit hyperactivity disorder, bipolar disorder). Pharmaceutical compositions and methods described herein may be used to ameliorate and/or inhibit one or more of the listed maladies and/or related maladies.

In some embodiments, a method or system described herein may include the measurement of a carrying capacity of a subject's blood. In some embodiments, a method or system described herein may measure a subject's defenses against chronic disease. In some embodiments, a method or system described herein may measure a subject's serum zeta potential. In some embodiments, a method or system described herein may measure a length of a subject's endothelial glycocalyx and/or the amount of particular substances known to be shed by a damaged endothelial glycocalyx in the subject's bloodstream. In some embodiments, a method or system described herein may measure the size of the boundary region of the endothelial surface layer in a subject's capillaries. A measurement of a subject's zeta potential and a subject's endothelial surface layer health may be used to determine a subject's Zeta Shield.

As regards the referenced hypercoagulation, a method may include a measurement of the subject's erythrocyte sedimentation rate (ESR). The erythrocyte sedimentation rate is a blood test which has been traditionally used to reveal inflammatory activity in the body. When a subject's blood is placed in a tall, thin tube, red blood cells (erythrocytes) gradually clump together and settle to the bottom of the tube. It is thought that inflammation can cause the cells to clump more quickly. Because these clumps are denser than individual cells, they settle to the bottom more quickly. The sedimentation rate test measures the distance red blood cells fall in a test tube in one hour. It is thought that the farther the red blood cells have descended, the greater the inflammatory response of a subject's immune system. However, herein it is known that the increased sedimentation rate may be a result of the reduction or loss of a subject's serum zeta potential and as such the test might be used to measure a subject's serum zeta potential.

There are several risk factors which may adversely affect a subject's zeta potential. In some embodiments, risk factors may include electromagnetic radiation, cigarette smoke, aluminum, heavy metals, radiocontrast agents, sugar, alcohol, poor nutrition, physical inactivity, bad stress, certain infectious diseases, serious cases of traumatic physical injury, and aging. In some embodiments, a method or system described herein may include administering compositions to inhibit and/or ameliorate adverse effects of one or more risk factors.

As described herein properties of the solution may affect the serum zeta potential. As such the blood serum pH can affect the serum zeta potential. If a subject's pH falls outside of standard parameters a composition may be administered to a subject to adjust the pH to within acceptable parameters. The pH of any fluid is the measure of the hydrogen ion ($H^-$) concentration. A pH of 7 is designated as neutral. The lower the pH, the more acidic the solution. It is accepted that a variety of factors affect blood serum pH, including but not limited to what is ingested, vomiting, diarrhea, lung function, endocrine function, kidney function, and urinary tract infection. A healthy subject's blood pH should be between about 7.35 and 7.45. In some embodiments, a method or system described herein may include administering compositions which function to optimize a subject's serum pH. Compositions designated for the optimization of blood serum pH may include calcium compounds, silica compounds, green food powders, silica, sources of bicarbonate, magnesium, chloride, sodium, potassium, olive leaf extract, and/or horsetail.

In some embodiments, compositions described herein may be formulated with a balance of electrolyte compounds designed to be maximally bioavailable, while simultaneously maintaining a high threshold of safety for consumption. The ingredients included in compositions described herein to ensure optimal serum zeta potential include magnesium chloride, sodium chloride, potassium chloride, olive leaf extract, and potassium citrate. The purpose of this composition is to ensure the bioavailability of sodium, potassium, chloride, and magnesium in the GI tract so that these compounds are readily available to ensure that gains such as increased serum albumin levels and chronic disease symptom remission are maintained and not lost.

In some embodiments, a method or system described herein may include compositions for maintaining and/or increasing a subject's serum zeta potential. The subject's serum zeta potential may be maximized by administering a composition to a subject which includes one or more salts. In some embodiments, a composition may include one or more halogen salts (e.g., chloride salts (e.g., magnesium chloride, potassium chloride, sodium chloride)). In some embodiments, a composition may include magnesium chloride. In some embodiments, a composition may include magnesium in one or more forms and chloride in one or more forms. Magnesium chloride may be used because of its bioavailability (i.e., solubility) and low toxicity. Chloride may be administered using olive plant extracts (e.g., olives, olive oil, olive leaf extract).

In some embodiments, a composition may be administered to a subject including potassium citrate in order to maximize a subject's serum zeta potential. Among other uses, potassium citrate may be used to treat metabolic problems (e.g., acidosis) caused by kidney disease. In some embodiments, a composition may be administered to a subject including sodium bicarbonate, potassium bicarbonate, potassium citrate, and/or magnesium bicarbonate, in order to optimize a subject's serum pH.

In some embodiments, a method or system described herein may include ensuring the health and safety of the endothelial surface layer. In some embodiments, a Zeta Shield of a subject may be maintained and/or repaired by maintaining and/or repairing a subject's endothelial surface layer, including the endothelial glycocalyx. The endothelial glycocalyx may function to hold the electrokinetic surface charge necessary to repel the plasma proteins and erythrocytes and prevent excessive perfusion and vascular permeability. The endothelial glycocalyx is the core component of the endothelial surface layer (ESL), which is generated by endothelial cells to modulate contact between abrasive serum elements and the endothelial cells themselves. The endothelial surface layer is responsible for vasodilation, which it prompts via nitrous oxide release in response to shear stress, as well as a net negative electric charge that allows for extremely rapid, low-friction blood flow and selective endothelial permeability.

Damage to a subject's endothelial surface layer occurs on a regular basis, due to any sort of wound or infection a subject can suffer. The endothelial surface layer may be eroded according to the process described herein termed as Endothelial Erosion (EE). A core component of the immune response is the enzymatic shedding of parts of the endothelial glycocalyx, which allows for extravasation of lymphocytes to the site of the wound. In some embodiments, compositions described herein facilitate healthy interaction between the serum and the endothelial surface layer by supplementing the nutritional intake of compounds which make up the endothelial surface layer (including the glycocalyx, which is composed of heparan sulfate, hyaluronic acid, glycosaminoglycans, and proteoglycans).

Compositions may include an endothelial augmentation component (e.g., Hyaluronic Acid, N-Acetyl Glucosamine, Glucosamine Sulfate, Chondroitin Sulfate, or Methylsulfonylmethane) designed to maximize the regenerative capacity of the endothelial surface layer. Hyaluronic acid is a component of the endothelial glycocalyx which may be supplemented in compositions to aid a subject's body's ability to recover from transient conditions in which endothelial surface layer health and function are impaired or to maximize the endothelial surface layer's capacity to produce and maintain the negative electric charge which allows it to maintain selective permeability.

N-Acetyl Glucosamine (NAG) is a precursor to hyaluronic acid. In some embodiments, compositions may contain NAG or other compounds to augment a subject's hyaluronic acid production. Glucosamine sulfate is a direct precursor to heparan sulfate, which makes up the side-chains of the protein strands which comprise the endothelial glycocalyx. Glucosamine sulfate or other compounds may be included in compositions to ensure the availability of the nutrients needed to heal a damaged endothelial surface layer. Chondroitin sulfate is a precursor to glycosaminoglycans which occur regularly in the endothelial glycocalyx. Chondroitin sulfate or other compounds may be included in described compositions to ensure the availability of the nutrients needed to heal a damaged endothelial surface layer.

In some embodiments, the endothelial surface layer may be maintained and/or repaired by administering a composition including one or more sulfur compounds. Sulfur compounds may include methylsulfonylmethane (MSM), heparan sulfate, glucosamine sulfate, glucosamine sulfate potassium, chondroitin sulfate, magnesium sulfate (Epsom salts), and/or N-acetyl glucosamine. The composition(s) may include compounds which contribute to the health of and/or form (or contribute to forming) of the endothelial glycocalyx including hyaluronic acid and/or collagen. Many of these compounds may be found in what is popularly known as "bone broth".

In some embodiments, a method or system described herein may include compositions for reversing or healing scarring, sclerosis, fibrosis, amyloidosis, calcification and/or plaque build-up which can occur as a result of the loss of a subject's serum zeta potential and the resulting damage referred to as Endothelial Erosion (EE)—to the endothelial surface layer that occurs as a result of adverse conditions including but not limited to the loss of serum zeta potential, physical trauma, infectious disease and/or toxic blood serum contents. Compositions for healing this damage may include methylsulfonylmethane, amino acids, dextrose, lipids, L-citrulline, DL-Malate, D-Ribose, serrapeptase, nattokinase, tocotrienols (e.g., delta, gamma), N-acetyl cysteine (NAC), vitamins (e.g., B-12, C, D, K), nitric oxide, beet root powder, iron, and/or zinc.

In some embodiments, a method or system described herein may include maintaining the serum's anti-coagulability and colloid osmotic pressure, resulting in an optimal serum zeta potential. Optimal and/or maximal serum zeta potential will reduce the occurrence of proteinuria. Compositions may include compounds which promote serum maintenance. Compounds may include, for example, methylsulfonylmethane, nattokinase, n-acetyl cysteine, lactoferrin, delta and gamma tocotrienols. Compositions described herein may include a serum maintenance group component designed to offer protection to the endothelial surface layer against damage due to stress, protect the serum itself from hypercoagulability, and ensure the correct range of serum zeta potential. For example, n-acetyl cysteine is a chemical responsible for vasodilation, which protects the endothelial glycocalyx from harm even under such adverse conditions as hyperglycemia. MSM may be included to deliver critical sulfates to the endothelial cells, assisting serum flow by providing a buffer which becomes active at the surface of the endothelial surface layer. Nattokinase is a synthetic fibrinolytic compound derived from fermented soy, and it helps to ensure that excessive coagulability in the serum is discouraged. Lactoferrin is a protein which may be included in compositions described herein to provide a reliable, non-glycated source of iron-binding protein while simultaneously increasing the concentration of negatively charged serum proteins. Delta & Gamma Tocotrienol (e.g., 90:10) may be included in compositions described herein as a further measure to provide antioxidant support to a subject's body while simultaneously boosting antithrombotic activity.

In some embodiments, a method or system described herein may include compositions to compensate or replenish bodily resources lost as a result of a loss of serum zeta potential leading to improper working of a subject's kidney. Healthy kidneys function to filter out bodily wastes from the blood stream but kidneys with a lower serum zeta potential or damaged endothelial surface layer as discussed herein allow proteins and other essential elements of the body to pass through and out the urinary tract. In some embodiments, a composition may be administered to a subject which includes one or more compounds (e.g., serum albumin, transferrin, lactoferrin, ceruloplasmin, amino acids, dextrose, lipids) typically at depleted levels due to malfunctioning kidneys. In some embodiments, a composition may be administered to a subject which includes one or more compounds to be used by a subject's body to naturally replace elements found at depleted levels due to malfunctioning kidneys. In some embodiments, a composition may be administered to a subject which includes one or more compounds (e.g., Epogen) which prompts a subject's body to naturally replace elements found at depleted levels due to malfunctioning kidneys.

In some specific embodiments, a method of treating proteinuria and/or related ailments discussed herein may include reestablishing optimal levels of essential plasma proteins lost due to proteinuria. This may include albumin infusions (e.g., 25 g every 8 hours as needed to keep serum albumin levels above 4.0 g/dL). Albumin infusions may make up for urinary losses of albumin, maintain system nutrient transport, and/or maintain oncotic pressure and limit toxicity, edema and ischemia.

In some specific embodiments, a method of treating proteinuria and/or related ailments discussed herein may include reestablishing optimal levels of transferrin lost due to proteinuria. This may include administering lactoferrin (e.g., 250 mg every 12 hours as needed to keep serum transferrin levels within an acceptable range) or even more optimally administering transferrin itself. Lactoferrin may help a subject's body make up for urinary losses of transferrin (the transport protein for iron) to limit oxidative stress from unbound iron and iron deficiency anemia.

In some specific embodiments, a method of treating proteinuria and/or related ailments discussed herein may include reestablishing maximal levels of a subject's serum zeta potential. In some embodiments, a subject may be administered magnesium chloride (e.g., 1500 mg every 8 hours). In some embodiments, a subject may be administered methylsulfonylmethane (e.g., 1000 mg every 8 hours). In some embodiments, a subject may be administered potassium citrate (e.g., 100 mg every 8 hours). In some embodiments, a subject may be administered magnesium chloride, methylsulfonylmethane, and potassium citrate. In some embodiments, a subject may be administered olive leaf extract (e.g., 750 mg every 12 hours). In some embodiments, a subject may be administered tocotrienol (e.g., 125 mg, 90% delta, 10% gamma, every 12 hours). In some embodiments, a subject may be administered magnesium chloride, methylsulfonylmethane, olive leaf extract, and tocotrienol.

In some embodiments, a subject's progress may be monitored during treatment. The subject's proteinuria may be monitored daily (e.g., by administering a urine test). As the subject's serum zeta potential is restored, the level of proteinuria will begin to decrease within days and will eventually reach the healthy level of albumin elimination (e.g., about 6% of daily albumin production).

In some embodiments, the subject's erythrocyte sedimentation rate may be monitored. The erythrocyte sedimentation rate will begin to fall within healthy parameters as the subject's serum zeta potential is restored.

In some embodiments, a method may include determining a subject's risk factor quotient by testing for a subject's Zeta Shield. The Zeta Shield may consist of a calculation based upon the mathematical combination of a subject's serum zeta potential score and a second score designed to reflect the health of a subject's endothelial surface layer (e.g., by measuring proximal biomarkers including but not limited to a subject's erythrocyte sedimentation rate, glycated albumin vs. total serum albumin and/or hemoglobin hbalc vs. total hemoglobin, blood pressure, circulating glycocalyx fragments, glycocalyx length, the average distance of perfusion of erythrocytes into the endothelial surface layer, the average endothelial permeability to albumin, etc.).

Dosage and Administration

In some embodiments, chemical compositions described herein may be administered at a dosage level up to conventional dosage levels, but will typically be less than about 50 mL per day. Suitable dosage levels for chemical compositions described herein may be about 0.01 mg to 10 mg per kg body weight of the patient per day, from about 0.1 mg to 1 mg per kg body weight of the patient per day, or from about 0.01 mg to 0.1 mg per kg body weight of the patient per day. The compound may be administered on a regimen of up to 6 times per day, between about 1 to 4 times per day, or once per day.

In the case where an oral composition is employed, a suitable dosage range is, e.g. from about 0.01 mg to about 10 mg per kg of body weight per day, preferably from about 0.1 mg to about 0.5 mg per kg.

It will be understood that the dosage of the therapeutic agents will vary with the nature and the severity of the condition to be treated, and with the particular therapeutic agents chosen. The dosage will also vary according to the age, weight, physical condition and response of the individual patient. The selection of the appropriate dosage for the individual patient is within the skills of a clinician.

In addition to administering chemical compositions described herein as described, the compounds may be administered as part of a pharmaceutical preparation containing suitable pharmaceutically acceptable carriers, preservatives, excipients and auxiliaries which facilitate processing of the chemical compositions described herein which may be used pharmaceutically. The preparations, particularly those preparations which may be administered orally and which may be used for the preferred type of administration, such as tablets, softgels, lozenges, dragees, and capsules, and also preparations which may be administered rectally, such as suppositories, as well as suitable solutions for administration by injection or orally or by inhalation of aerosolized preparations, may be prepared in dose ranges that provide similar bioavailability as described above, together with the excipient. While individual needs may vary, determination of the optimal ranges of effective amounts of each component is within the skill of the art.

General guidance in determining effective dose ranges for pharmacologically active compounds and compositions for use in the presently described embodiments may be found, for example, in the publications of the International Conference on Harmonisation and in REMINGTON'S PHARMACEUTICAL SCIENCES, $8^{th}$ Edition Ed. Bertram G. Katzung, chapters 27 and 28, pp. 484-528 (Mack Publishing Company 1990) and yet further in BASIC & CLINICAL PHARMACOLOGY, chapters 5 and 66, (Lange Medical Books/McGraw-Hill, New York, 2001).

Pharmaceutical Compositions

Chemical compositions described herein are typically administered orally but any suitable route of administration may be employed for providing a subject with an effective dosage of drugs of the chemical compositions described herein. For example, oral, rectal, topical, parenteral, ocular, pulmonary, nasal, and the like may be employed. Dosage forms include tablets, troches, dispersions, suspensions, solutions, capsules, creams, ointments, aerosols, and the like. In certain embodiments, it may be advantageous that the compositions described herein be administered orally (e.g., tablets, capsules, softgels, solutions, suspensions, etc.).

The compositions may include those compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the drugs used in the present invention are conveniently delivered in the form of an aerosol spray presentation from pressurized packs or nebulizers. The compounds may also be delivered as powders which may be formulated and the powder composition may be inhaled with the aid of an insufflation powder inhaler device.

Suitable topical formulations for use in the present embodiments may include transdermal devices, aerosols, creams, ointments, lotions, dusting powders, gels, and the like.

In practical use, drugs used can be combined as the active ingredient in intimate admixtures with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, pharmaceutical media may be employed. For example, in the case of oral liquid preparations (e.g., suspensions, elixirs and solutions) pharmaceutical media may include water, glycols, oils, alcohols, flavoring agents, preservatives, coloring agents and the like. For example, in the case of oral solid preparations (e.g., powders, capsules and tablets) pharmaceutical media may include carriers such as starches, sugars, microcrystalline cellulose, diluents, granulating agents, lubricants, binders, disintegrating agents and the like. In some embodiments, the solid oral preparations are preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

The pharmaceutical preparations may be manufactured in a manner which is itself known to one skilled in the art, for example, by means of conventional mixing, granulating, dragee-making, softgel encapsulation, dissolving, extracting, or lyophilizing processes. Thus, pharmaceutical preparations for oral use may be obtained by combining the active compounds with solid and semi-solid excipients and suitable preservatives. Optionally, the resulting mixture may be ground and processed. The resulting mixture of granules may be used, after adding suitable auxiliaries, if desired or necessary, to obtain tablets, softgels, lozenges, capsules, or dragee cores.

The compounds are typically administered in admixture with suitable pharmaceutical diluents, excipients, or carriers (collectively referred to herein as "pharmacologically inert carriers") suitably selected with respect to the intended form of administration, that is, oral tablets, capsules, elixirs, syrups and the like, and consistent with conventional pharmaceutical practices.

Suitable excipients may be fillers such as saccharides (e.g., lactose, sucrose, or mannose), sugar alcohols (e.g., mannitol or sorbitol), cellulose preparations and/or calcium phosphates (e.g., tricalcium phosphate or calcium hydrogen phosphate). In addition binders may be used such as starch paste (e.g., maize or corn starch, wheat starch, rice starch, potato starch, gelatin, tragacanth, methyl cellulose, hydroxypropylmethylcellulose, sodium carboxymethylcellulose, and/or polyvinyl pyrrolidone). Disintegrating agents may be added (e.g., the above-mentioned starches) as well as carboxymethyl-starch, cross-linked polyvinyl pyrrolidone, agar, or alginic acid or a salt thereof (e.g., sodium alginate). Auxiliaries are, above all, flow-regulating agents and lubricants (e.g., silica, talc, stearic acid or salts thereof, such as magnesium stearate or calcium stearate, and/or polyethylene glycol, or PEG). Dragee cores are provided with suitable coatings, which, if desired, are resistant to gastric juices. Softgelatin capsules ("softgels") may be provided with suitable coatings, which, typically, contain gelatin and/or suitable edible dye(s). Animal component-free and kosher gelatin capsules may be particularly suitable for the embodiments described herein for wide availability of usage and consumption. For this purpose, concentrated saccharide solutions may be used, which may optionally contain gum arabic, talc, polyvinyl pyrrolidone, polyethylene glycol (PEG) and/or titanium dioxide, lacquer solutions and suitable organic solvents or solvent mixtures, including dimethylsulfoxide (DMSO), tetrahydrofuran (THF), acetone, ethanol, or other suitable solvents and co-solvents. In order to produce coatings resistant to gastric juices, solutions of suitable cellulose preparations such as acetylcellulose phthalate or hydroxypropylmethyl-cellulose phthalate, may be used. Dyes or pigments may be added to the tablets or dragee coatings or softgelatin capsules, for example, for identification or in order to characterize combinations of active compound doses, or to disguise the capsule contents for usage in clinical or other studies.

Other pharmaceutical preparations that may be used orally include push-fit capsules made of gelatin, as well as soft, thermally sealed capsules made of gelatin and a plasticizer such as glycerol or sorbitol. The push-fit capsules may contain the active compounds in the form of granules that may be mixed with fillers such as, for example, lactose, binders such as starches, and/or lubricants such as talc or magnesium stearate and, optionally, stabilizers and/or preservatives. In soft capsules, the active compounds may be dissolved or suspended in suitable liquids, such as fatty oils such as rice bran oil or peanut oil or palm oil, or liquid paraffin. In some embodiments, stabilizers and preservatives may be added.

Liquid dosage forms for oral administration can contain coloring and flavoring to increase subject acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

In some embodiments, an oral composition may include a flavoring. A flavoring may include something a subject may find palatable. For example, a flavoring may include malt extract, Xylitol, Splenda, sucralose or any sweetener. A flavoring may range from 0.01% to 0.10%, 0.10% to 1.0%, or 1.0% to 10.0% of a composition.

In some embodiments, a composition may include a colorant. A colorant may include D&C Blue #1 or any FDA approved color. A colorant may range from 0.001% to 0.010%, 0.010% to 0.10%, or 0.10% to 1.0% of a composition.

Additional oral compositions which may be used to deliver chemical compositions described herein, as well as additional uses, are described in U.S. Pat. No. 4,666,896 to Warner, Jr. et al., U.S. Pat. No. 5,393,516 to Rheinberger et al., and U.S. Pat. No. 5,948,390 to Nelson et al., as well as U.S. Patent Publication No. 2005/0158252 to Romanowski et al., which are incorporated by reference as if fully set forth herein.

In some embodiments, pulmonary administration of a pharmaceutical preparation may be desirable. Pulmonary administration may include, for example, inhalation of aerosolized or nebulized liquid or solid particles of the pharmaceutically active component dispersed in and surrounded by a gas. Possible pharmaceutical preparations, which may be used rectally, include, for example, suppositories, which consist of a combination of the active compounds with a suppository base. Suitable suppository bases are, for example, natural or synthetic triglycerides, or paraffin hydrocarbons. In addition, it is also possible to use gelatin rectal capsules that consist of a combination of the active compounds with a base. Possible base materials include, for example, liquid triglycerides, polyethylene glycols, or paraffin hydrocarbons.

Suitable formulations for parenteral administration may include, but are not limited to, suspensions of the active compounds. Suitable lipophilic solvents, co-solvents (such as DMSO or ethanol), and/or vehicles including fatty oils, for example, rice bran oil or peanut oil and/or palm oil, or synthetic fatty acid esters, for example, ethyl oleate or triglycerides, may be used. Liposomal formulations, in which mixtures of the chemical compositions described herein with, for example, egg yolk phosphotidylcholine (E-PC), may be made for injection. Optionally, the suspension may contain stabilizers, for example, antioxidants such as BHT, and/or preservatives, such as benzyl alcohol.

In some embodiments, an oral composition may include a fragrance.

In some embodiments, a composition may include additional additives which may function in combination or separately from the chemical compositions described herein in solution. Additives may function to improve a subject's health. Additives may include vitamins including, but not limited to, vitamins D and E.

In some embodiments, different compositions may be formulated for different types of users. For professional users (e.g., doctors, veterinarians), compositions may include a greater percentage of chemical compositions described herein than compositions formulated for over the counter sale to nonprofessionals. Professional compositions may not include flavorings or colorants.

While previous discussions herein have concentrated on the use of chemical compositions described herein for treating maladies associated with oral cavities of humans and animals. Chemical compositions described herein may be used for the inhibition and/or amelioration of various maladies associated with humans and/or more particularly animals.

While previous discussions herein have concentrated on the use of chemical compositions and methods described herein for treating maladies associated with humans, this example should not be seen as limiting. Compositions described herein may be used to treat other animals (e.g., mammals) including, but not limited to, felines, canines, avians (birds), reptiles, horses, swine, sheep, goats, deer, tigers, protein producing animals (e.g., cattle), and/or lions.

EXAMPLES

Having now described the invention, the same will be more readily understood through reference to the following example(s), which are provided by way of illustration, and are not intended to be limiting of the present invention.

Case Study 1: Zeta Biolongevity, Inc., has developed the initial version of ZB10.1 which has already been shown to reduce the level of proteinuria in the ongoing early stages of the initial trial. The first test subject, a feline named Claire, had significant proteinuria as shown by her average urine protein/creatinine ratio (UPC), which was >0.5 at the beginning of testing, which has diminished significantly during the first few months of treatment. As kidney disease is thought to be degenerative, the reduction in proteinuria is a promising sign that treatment has been effective.

Claire is a 9-year old female feline who is non-azotemic with severe proteinuria. She has had a chronic upper respiratory infection (URI) for most of her life. The URI, prior to treatment, was very severe incessant sneezing, heavy mucous drip, congestion, hacking/choking. She was very lethargic and had a poor appetite. Within weeks of treatment, her URI symptoms have improved significantly. Her breathing is clearer, her nose does not run as much, and her appetite has improved substantially. Additionally, Claire's urine PH improved from 7 or higher (outside of healthy range) to 6-6.5 (inside healthy range). Claire has significant increase in energy, sociability and appetite. Claire is entering her $3^{rd}$ month of treatment. It is anticipated she will continue to require ongoing treatment for least 6 more months, due to her long history of multiple chronic ailments.

Claire's average proteinuria score before the beginning of trials was 0.6667. Since the beginning of treatment, it has declined to 0.2, which is non-proteinuric according to IRIS guidelines. FIGS. 20-21 depict a spreadsheet showing the preliminary results achieved by treating a cat with severe proteinuria with compositions described herein. The Zeta Theory of Proteinuria & Endothelial Erosion predicts a relationship between serum chemistry and proteinuria.

Claire was administered ZB10.1 during treatment, the components of which are detailed in TABLE 1 (in some embodiments, percentages in TABLE 1 may be +/−10%). ZB10.1 has been developed to ensure that every aspect of Serum Zeta Potential can be maintained. ZB10.1 ensures that the negatively charged endothelial surface layer is able to repel abrasive plasma proteins and erythrocytes throughout the system, but particularly in the glomerulus. When this relationship breaks down, proteinuria is one result. Hence, a reduction in proteinuria is a significant confirmation of the underlying theory as well as an indication that ZB10.1 is effective.

TABLE 1 mg/day 650
capsules/day 2
mg/capsule 325

| Ingredient | % | mg/day | mg/capsule | Maximize Serum Zeta Potential | Maximize Health of Endothelial Surface Layer | Make up for Urinary Losses | Maximize Blood Flow & Heal/Repair Damage |
|---|---|---|---|---|---|---|---|
| Magnesium Chloride | 5.0% | 32.7 | 16.3 | X | | X | |
| Potassium Chloride | 10.1% | 65.3 | 32.7 | X | | X | |
| Sodium Chloride | 10.1% | 65.3 | 32.7 | X | | X | |
| Potassium Citrate | 2.5% | 16.3 | 8.2 | X | | | |
| Olive Leaf Extract | 15.1% | 98.0 | 49.0 | X | | | |
| MSM | 15.1% | 98.0 | 49.0 | | X | | X |
| Chondroitin sulfate | 10.1% | 65.3 | 32.7 | | X | | |
| Glucosamine sulfate | 10.1% | 65.3 | 32.7 | | X | | |
| N-A-G | 5.0% | 32.7 | 16.3 | | X | | |
| Hyaluronic Acid | 2.5% | 16.3 | 8.2 | | X | | |
| N-Acetyl Cysteine | 5.0% | 32.7 | 16.3 | | X | | X |
| Lactoferrin | 5.0% | 32.7 | 16.3 | | | X | |
| Tocotrienols | 2.5% | 16.3 | 8.2 | | | | X |
| Nattokinase | 2.0% | 13.1 | 6.5 | | | | X |
| Totals | 100.0% | 650.0 | 325.0 | | | | |

Case Study 2: In September 2014, Randy Thompson was 54 years old and in excellent health with none of the lifestyle risk factors or metabolic risk factors currently presumed to be the root causes of our global epidemic of chronic disease. Then, on Sep. 19, 2014, Randy Thompson suddenly had massive proteinuria. Within two weeks, his serum albumin dropped to 1.7 and he was diagnosed with Minimal Change Disease (MCD). Despite high doses of all the usual corticosteroids, anti-inflammatories, immunosuppressants, diuretics, etc., he progressed to End Stage Renal Disease (ESRD) in less than 12 months (Creatinine 6.24, BUN 130) and started hemodialysis.

Randy Thompson also developed all the comorbidities associated with diabetes (peripheral artery disease, peripheral neuropathy, retinopathy, systemic scarring, sclerosis, fibrosis, etc.) without ever having diabetes or hyperglycemia. His total cholesterol increased to 550 and he developed over 70 pounds of severe pitting edema.

While on dialysis for 8 months waiting for a kidney transplant (3.5-5.5 liters of fluid removed every MWF), Randy Thompson identified the underlying root cause of proteinuria and the mechanism of progression to ESRD and all related metabolic, vascular and neurological comorbidities. To end dialysis Randy Thompson began self-administering magnesium chloride, methylsulfonylmethane, olive leaf extract, and tocotrienols (delta and gamma). Further Randy Thompson self-administered potassium citrate, chondroitin sulfate, glucosamine sulfate, and hyaluronic acid. After dialysis he received albumin infusions to make up for urinary losses of albumin until his kidneys had a chance to heal. Randy Thompson began self-administering lactoferrin to ameliorate severe iron deficiency anemia due to urinary losses of transferrin.

After months of treatment, it became apparent that Randy Thompson had been able to reverse and cure his ESRD and all the associated comorbidities. Randy Thompson has now fully recovered and has normal kidney function once again. Randy Thompson has also restored all the blood flow to his legs, ankles and feet and has healed all the peripheral nerve damage.

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method to alleviate proteinuria in a human patient by reducing permeability of the vascular endothelial surface layer comprising:

1) orally administering a component of vascular endothelial glycocalyx comprising hyaluronic acid;
2) orally administering lactoferrin in an amount effective to increase serum levels of transferrin;
3) increasing serum zeta potential by orally administering a composition comprising a pharmaceutically effective amount of chondroitin and glucosamine to reduce hypercoagulation of erythrocytes;
4) administering albumin intravenously;
5) administering a sulfur compound selected from the group consisting of methylsulfonylmethane (MSM), heparan sulfate, magnesium sulfate, N-acetyl glucosamine, a sulfur derivative of the chondroitin, a sulfur derivative of the glucosamine, and combinations thereof; and
6) achieving a therapeutically effective decrease in urinary protein.

2. The method of claim 1, wherein the patient is in need of treatment for nephrotic syndrome.

3. The method of claim 1, further comprising the administration of methylsulfonylmethane to ameliorate damage to the vascular endothelial surface layer.

4. The method of claim 1 further comprising the administration of tocotrienols.

5. The method of claim 4, wherein the tocotrienols comprise delta and gamma tocotrienols in a 90:10 ratio respectively.

6. The method of claim 1, further comprising the administration of a compound selected from the group consisting of nattokinase, potassium citrate, and olive leaf extract and combinations thereof.

7. The method of claim 1 further comprising administering N-acetyl cysteine.

8. The method of claim 1 further comprising administering magnesium.

9. The method of claim 1 further comprising measuring an erythrocyte sedimentation rate in the human patient.

10. The method of claim 1, wherein the hyaluronic acid, glucosamine, chondroitin and lactoferrin are administered in a pharmaceutical composition combined in a predetermined unit dose effective to decrease excess urinary protein excretion.

* * * * *